(12) United States Patent
Dambinova et al.

(10) Patent No.: US 7,820,398 B2
(45) Date of Patent: Oct. 26, 2010

(54) IMMUNOSORBENT BLOOD TESTS FOR ASSESSING PAROXYSMAL CEREBRAL DISCHARGES

(75) Inventors: Svetlana A. Dambinova, Atlanta, GA (US); Galina Izykenova, Atlanta, GA (US)

(73) Assignee: Grace Laboratories Inc., Atlanta, GA (US)

( * ) Notice: Subject to any disclaimer, the term of this patent is extended or adjusted under 35 U.S.C. 154(b) by 0 days.

(21) Appl. No.: 10/983,845

(22) Filed: Nov. 8, 2004

(65) Prior Publication Data

US 2005/0181466 A1 Aug. 18, 2005

Related U.S. Application Data

(60) Provisional application No. 60/517,671, filed on Nov. 6, 2003.

(51) Int. Cl.
G01N 33/566 (2006.01)
G01N 33/49 (2006.01)
G01N 33/50 (2006.01)

(52) U.S. Cl. ..................... 435/7.21

(58) Field of Classification Search ............... None
See application file for complete search history.

(56) References Cited

U.S. PATENT DOCUMENTS

| | | | | | |
|---|---|---|---|---|---|
| 4,879,289 | A | * | 11/1989 | Zobrist et al. | 514/211.07 |
| 5,739,291 | A | * | 4/1998 | Heinemann et al. | 530/388.22 |
| 6,896,872 | B2 | | 5/2005 | Dambinova | |
| 2005/0233390 | A1 | * | 10/2005 | Allen | 435/7.9 |
| 2006/0024749 | A1 | | 2/2006 | Dambinova | |
| 2006/0172341 | A1 | | 8/2006 | Dambinova | |
| 2006/0172342 | A1 | | 8/2006 | Dambinova | |
| 2006/0257943 | A1 | | 11/2006 | Dambinova | |

FOREIGN PATENT DOCUMENTS

| | | |
|---|---|---|
| EP | 0558747 A1 | 9/1993 |
| RU | 2112243 C1 | 5/1998 |
| WO | WO 93/00586 A1 | 1/1993 |
| WO | WO 94/06345 A2 | 3/1994 |

OTHER PUBLICATIONS

Producing Polyclonal Antibodies. (downloaded Sep. 14, 2006) Gallus immunotech, inc. pp. 1-2.*
Nath et al. (2000). Neurochem int. 37, 351-61. Abstract only.*
Williamson et al (1992). Ann. Neurol. 31, 3-13. Abstract only.*
Sviridova et al. (1990) Zh. Nevrapato Psikhiatr. Im S S Korsakova. 90, 3-5. Abstract only.*
Radhadrishnan et al. (1981). Clin Neurol. Neurosurg. 83, 87-94. abstract only.*
Stigbrand et al. (2000). Int J. Biol. Markers 15, 33-40. Abstract only.*
Morozov et al. (1996). Zh. Nevrapato Psikhiatr. Im S S Korsakova. 96, 71-74. Abstract only.*
Dambinova et al (1998). J. Neurochem. 71, 2088-2093.*
Dambinova et al. (1997) J. neurochem. 152, 93-97.*
Hornbeck (1991. Current Protocols in Molecular Biology 11.2.1 - 11.2.22).*
Andrews, P.I., and McNamara, J.O., "Rasmussen's encephalitis: an autoimmune disorder?," *Curr. Opin. Neurol.*, 9(2):141-145 (Apr. 1996).
Andrews, P.I., et al., "Plasmapheresis in Rasmussen's encephalitis," *Neurology*, 46(1):242-246 (Jan. 1996).
Bellinger, D.C., et al., "Developmental and neurological status of children at 4 years of age after heart surgery with hypothermic circulatory arrest or low-flow cardiopulmonary bypass," *Circulation*, 100(5):526-532 (Aug. 3, 1999).
Besedin, V.I., et al., "Molecular organization of glutamate-sensitive chemoexcitable membranes of nerve cells. Function of glutamate-binding proteins of the central nervous system when incorporated into liposomes", *Chem. Abstr.*, 102:198497h (1985) (abstract of Russian-language *Biokhimiia*, 50(3):363-368 (Mar. 1985)).
Bi, X., et al., "Characterization of calpain-mediated proteolysis of GluR1 subunits of alpha-amino-3-hydroxy-5-methylisoxazole-4-propionate receptors in rat brain," *J. Neurochem.*, 68(4):1484-1494 (Apr. 1997).
Bi, X., et al., "The C-terminal domain of glutamate receptor subunit 1 is a target for calpain-mediated proteolysis," *Neuroscience*, 73(4):903-906 (Aug. 1996).
Boulter, J., et al., "Molecular cloning and functional expression of glutamate receptor subunit genes.," *Science*, 249(4972):1033-1037 (Aug. 31, 1990).
Cleary, P., et al., "Late-onset seizures as a predictor of subsequent stroke," *Lancet* 363(9416):1184-1186 (Apr. 10, 2004).
Dambinova, S.A. et al., "Molecular organization of glutamate-sensitive chemoexcitatory membranes of nerve cells. Comparative analysis of glutamate-binding membrane proteins from the cerebral cortex of rats and humans,", *Chem. Abstr.*, 108:51550k (1988) (abstract of Russian-language *Biokhimiia*, 52(10):1642-1648 (Oct. 1987)).
Dambinova, S.A., and Gorodinskii, A.I., "Molecular organization of the glutamate-sensitive chemoexcitatory membranes of nerve cells. L-[$^3$H]Glutamate binding to synaptic membranes from the rat cerebral cortex," *Chem. Abstr.*, 100:133097s (1984) (abstract of Russian-language *Biokhimiia*, 49(1):67-74 (Jan. 1984)).
Dambinova, S.A., and Izykenova, G.A., "Autoantibodies to subtypes of glutamate receptors as a hallmarks [sic] of brain damage: diagnostic significance for paroxysmal activity and ischemia", *J. Higher Nervous Activity* [Zh. Vyssh. Nerv. Deiat. Im. I.P. Pavlova], 47(2):151-156 [439-446 in original Russian version] (Mar.-Apr. 1987).

(Continued)

*Primary Examiner*—Daniel E. Kolker
(74) *Attorney, Agent, or Firm*—Clark G. Sullivan; Arnall Golden Gregory LLP

(57) ABSTRACT

Immunosorbents, kits and compositions for diagnosing a central nervous system disorder, particularly paroxysmal cerebral discharges and epilepsy, comprising measuring the concentration of GluR1 or fragment thereof and/or GluR1 antibodies in a biological sample from a human subject. The method is particularly useful for identifying individuals that are at risk for brain related seizures and epilepsy, for distinguishing epilepsy from pseudo-epilepsy and epilepsy-like disorders, for following up after anticonvulsive treatment, and for the adjustment of adequate therapy and doses.

21 Claims, 2 Drawing Sheets

Dambinova, S.A., et a/., "Molecular organization of glutamate-sensitive, chemoexcitatory membranes of nerve cells. Physicochemical characteristics of the glutamate-binding chemoexcitatory membrane proteins from rat cerebral cortex synamptic membranes", *Chem. Abstr.*, 100:152673t (1984) (Abstract of Russian-language *Biokhimiia*, 49(2):216-221 (Feb. 1984)).

Dambinova, S.A., et al., "Blood test detecting autoantibodies to N-methyl-D-aspartate neuroreceptors for evaluation of patients with transient ischemic attack and stroke," *Clin. Chem.*, 49(10):1752-1762 (2003).

Dambinova, S.A., et a, "Immunochemical electron microscopic study of glutamate receptor localization in cultured cells of the *Rattus rattus* brain sensorimotor cortex using monoclonal antibodies," *Chem. Abstr.*, 111:71506r (1989) (abstract of Russian-language *Biol. Membr.*, 6:498-506 (1989)).

Dambinova, S.A., et a/., "Immunosorbent for diagnosis of epilepsy and risk group," *Chem. Abstr.*, 118:100345q (1993) (abstract of Russian-language patent publication WO 93/00586 by Dambinova et al. and Dies Co., Ltd, published Jan. 7, 1993).

Dingledine, R., "The glutamate receptor ion channels," et al., *Pharmacol. Rev.*, 51(1):7-61 (Mar. 1999).

Dingledine, R., and McBain, C.J., "Glutamate and Aspartate," Chap. 15 in *Basic Neurochemistry: Molecular, Cellular and Medical Aspects*, 6$^{th}$ed, Siegel, G.J., et al., Eds., Philadelphia, Pa.: Lippincott-Raven; (1999), 315-333.

Doherty, J., and Dingledine, R., "Reduced excitatory drive onto interneurons in the dentate gyrus after status epilepticus," *J. Neurosci.*, 21(6):2048-2057 (Mar. 15, 2001).

During, M.J., et al., "An oral vaccine against NMDAR1 with efficacy in experimental stroke and epilepsy," *Science*, 287(5457):1453-1460 (Feb. 25, 2000).

Fagan, A.M., and Gage, F.H., "Mechanisms of sprouting in the adult central nervous system: cellular responses in areas of terminal degeneration and reinnervation in the rat hippocampus," *Neuroscience*, 58(4):705-725 (Feb. 1994).

Fletcher, E.J., et al., "Cloning, expression and pharmacological characterization of a human glutamate receptor: hGluR4," *Receptors Channels* 3(1):21-31 (1995).

Friedman, L.K., et al., "Kainate-induced status epilepticus alters glutamate and GABAA receptor gene expression in adult rat hippocampus: an in situ hybridization study," *J. Neurosci*, 14(5 Pt 1):2697-2707 (May 1994).

Gahring, L.C., et al., "Autoantibodies to neuronal glutamate receptors in patients with paraneoplastic neurodegenerative syndrome enhance receptor activation," *Mol. Med*, 1(3):245-253 (Mar. 1995).

Gingrich, M.B., and Traynelis, S.F., "Serine proteases and brain damage—is there a link?" *Trends Neurosci.*, 23(9):399-407 (Sep. 2000).

Grigorenko, E., "Changes in glutamate receptor subunit composition in hippocampus and cortex in patients with refractory epilepsy," et al., *J. NeuroL Sci.*, 153(1):35-45 (Dec. 9, 1997).

Huppertz, H.-G.,et al., "Myoclonus in epilepsy patients with anticonvulsive add-oon therapy with pregablalin," *Epilepsia*, 42(6):790-792 (2001), provided as abstract.

Kopeloff, L.M., et al., "Recurrent convulsive seizures in animals produced by immunologic and chemical means," *Am. J. Psychiatry*, 98:881-902 (1942).

Maslova, O.I. et al., "[Paroxysmal activity test in pediatric neurology]," *Zh. Nevrol. Psikhiatr. Im. S. S. Korsakova*, 98(1):33-36 (1998) (in Russian); provided as English-language abstract.

Meldrum, B.S., "Glutamate as a neurotransmitter in the brain: review of physiology and pathology," *J. Nutr.*, 130(4S Suppl.):1007S-1015S (Apr. 2000).

Nicole, O., et al., "The proteolytic activity of tissue-plasminogen activator enhances NMDA receptor-mediated signaling," *Nature Med.*, 7(1):59-64 (Jan. 2001).

Nitsch, C., et al., "Pathophysiological aspects of blood-brain barrier permeability in epileptic seizures," *Adv. Exp. Med. Biol.*, 203:175-189 (1986).

Orlova, E.A., et al., "Human brain glutamate receptors visualized by monoclonal antibodies,", *Chem. Abstr.*, 111:147323b (1989) (abstract of Russian-language *Dokl. Akad. Nauk SSSR*, 307(2):495-496 (1989)).

Potier, M.C., Human GluR1 receptor protein sequence, Accession No. CAA41491, NCBI Entrez Protein database (sequence submitted Nov. 9, 1993).

Puckett, C., et al., "Molecular cloning and chromosomal localization of one of the human glutamate receptorgenes," *Proc. Natl. Acad. Sci. U.S.A.* 88(17):7557-7561 (Sep. 1, 1991).

Rampersad, V., et al., "Human glutamate receptor hGluR3 flip and flop isoforms: cloning and sequencing of the cDNAs and primary structure of the proteins." *Biochim. Biophys. Acta* 1219(2):563-566 (Oct. 18, 1994).

Rogers, S.W., et al., "Autoantibodies to glutamate receptor G1uR3 in Rasmussen's encephalitis," *Science*, 265(5172):648-651 (Jul. 29, 1994).

Smirnova, T.M., et al., "Cloning of the cDNA fragment of the human brain kainate receptor," *Chem. Abstr.*, 112:49962k (1990) (abstract of Russian-language *Dokl. Akad. Nauk SSSR*, 309(3):745-748 (1989)).

Smirnova, T.M., et al., "Isolation and study of cDNA coding for the synthesis of glutamate receptors of human brain"], *Chem. Abstr.*, 110:70440g (1989) (abstract of Russian-language *Dokl. Akad. Nauk SSSR*, 303(3):756-759 (1988)).

Sternberg, E.M., "Interactions between the immune and neuroendocrine systems," *Progress in Brain Research*, 122:35-42 (2000).

Sun, W., et al., "Primary structure and functional expression of the AMPA/kainate receptor subunit 2 from human brain," *NeuroReport*, 5(4):441-444 (Jan. 12, 1994).

Twyman, R.E., et al., "Glutamate receptor antibodies activate a subset of receptors and reveal an agonist binding site," *Neuron*, 14(4):755-762 (Apr. 1995).

Vincent, a., et al., "Pathogenic autoantibodies to neuronal proteins in neurological disorders," *J. Neuroimmunol.*, 100(1-2):169-180 (Dec. 1999).

Whetsell, W.O., Jr., "Current concepts of excitotoxicity," *J. Neuropathol Exp. Neurol.*, 55(1):1-13 (Jan. 1996).

* cited by examiner

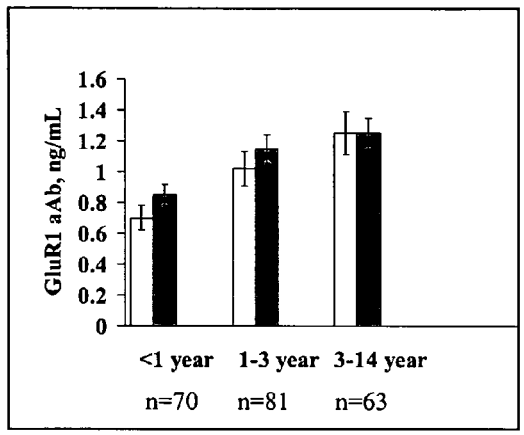

Fig. 1. GluR1 autoantibodies amounts in blood serum of healthy children (white bars) and those with non-epileptic disorders (shaded bars) depending on age.

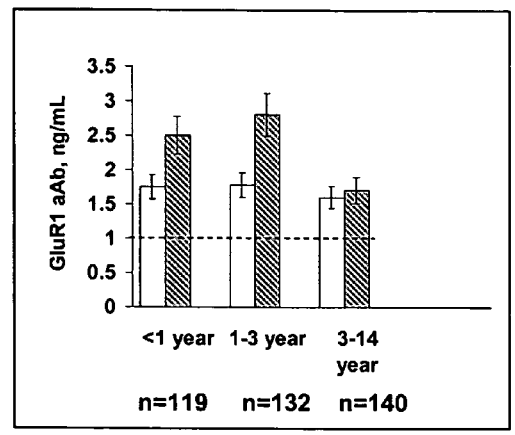

Fig. 2. GluR1 autoantibodies in blood serum of children with epilepsy syndrome (white bars) and epilepsy (stroked bars). Dotted line shows the cut off for GluR1 aAb.

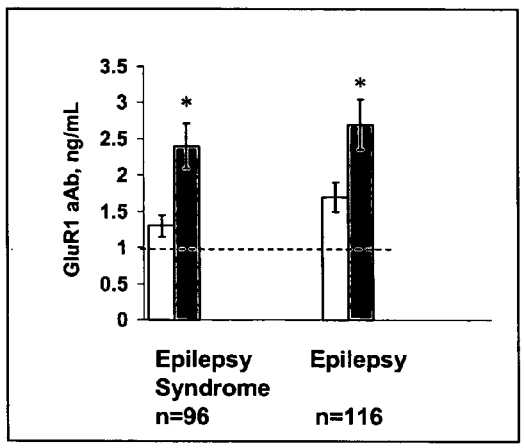

Fig. 3. GluR1 autoantibodies in blood serum of children with partial (white bars) and generalized seizures (shaded bars). Dotted line shows the cut off for GluR1 aAb.

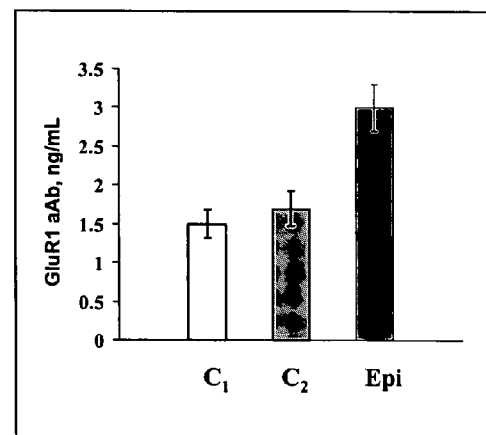

Fig. 4. Detection of GluR1 aAb in blood serum of healthy persons ($C_1$), patients with non-epileptic neurological disorders ($C_2$) and patients with epilepsy (Epi).

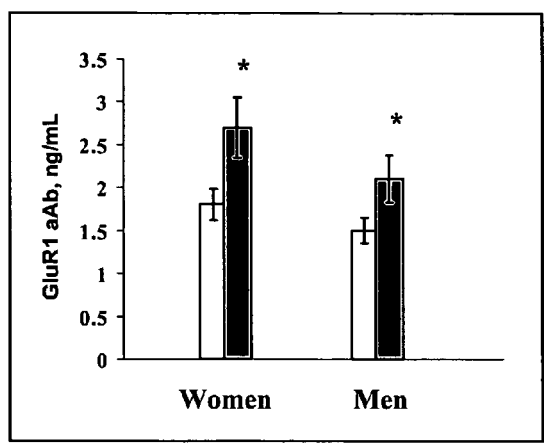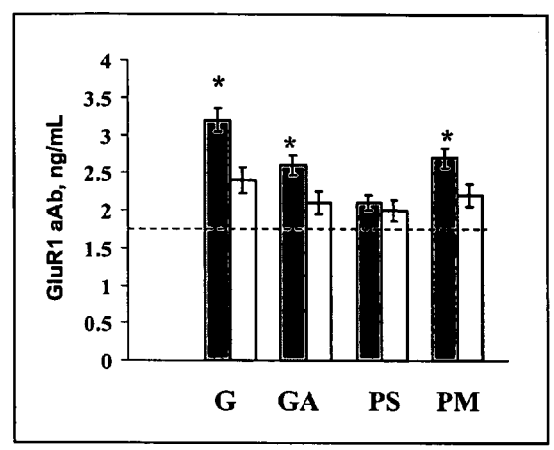
Fig. 5. GluR1 aAb dependence from gender: in total controls (white bars) and patients with epilepsy (shaded bars).
Fig. 6. GluR1 aAb dependence from seizures type and frequency: dark bars – daily seizures; light bars – 1 per half year. G– generalized tonic-clonic (n=98); GA – generalized with absences (n=50); PS – partial simple (n=33) and PM – partial multiple (n=56).

ial tests, particularly immuno- and proteomic tests, for diagnosing and assessing the risk associated with nervous and mental diseases. The tests detect specific brain markers of neurotoxicity, evaluate toxicological and neurological brain damage, and assist in the diagnosis, therapy and management of brain disorders.
IMMUNOSORBENT BLOOD TESTS FOR ASSESSING PAROXYSMAL CEREBRAL DISCHARGES

RELATION TO PRIOR APPLICATIONS

This application claims priority to U.S. Provisional Application No. 60/517,671, filed Nov. 6, 2003.

FIELD OF THE INVENTION

The present invention relates to clinical in-vitro diagnostic tests, particularly immuno- and proteomic tests, for diagnosing and assessing the risk associated with nervous and mental diseases. The tests detect specific brain markers of neurotoxicity, evaluate toxicological and neurological brain damage, and assist in the diagnosis, therapy and management of brain disorders.

BACKGROUND

Epilepsy is a disease characterized by epileptic seizures—generally defined as those seizures caused by a brief disruption of brain function involving temporary abnormal electrical activity in the nerve cells. The location of this disruption in the brain determines the type of seizure. Epilepsy should be contrasted with syncope which, although both frequently result in unconsciousness, syncope refers to a loss of consciousness due to transient impairment of cerebral blood flow.

The two main types of epileptic seizures are partial and generalized. Partial seizures involve part of the brain, while generalized seizures involve the whole brain. Partial seizures can become generalized seizures if the epileptic activity spreads to the whole brain.

Many people are born with epilepsy. In other cases, epilepsy develops as a result of brain damage from other disorders. For example, brain tumors, head injury, alcoholism, and Alzheimer's disease frequently lead to epilepsy because they alter the normal workings of the brain. Strokes, heart attacks, and other conditions that deprive the brain of oxygen also can cause epilepsy in some cases. About 32% of all newly developed epilepsy in elderly people appears to be due to cerebrovascular disease. Meningitis, AIDS, viral encephalitis, and other infectious diseases can lead to epilepsy, as can hydrocephalus—a condition in which excess fluid builds up in the brain.

Epileptiform activity usually begins in vivo with excessive AMPA receptor activation; as the seizure activity intensifies, an increased involvement of NMDA receptors is observed (Dingledine, McBain, *Basic Neurochemistry*. Philadelphia, Pa.: Lippincott-Raven; 1998, 315-333). Over activation of NMDA and AMPA receptors allows excessive $Ca^{2+}$ influx into the cell resulting in activation of many enzymes and proteases, which begin to destroy the components of the cell membrane. That includes different Ca++ activated enzymes, including calmodulin-dependent protein kinase, calcineurin, calpain, PKS, phospholipase and number of endonucleases (Whetsell J. Neuropathol. Exp. Neurol. 1996; 55:1-13).

Seizures from epilepsy can take a number of forms. Generalized seizures include "tonic-clonic," "absence," "atonic," and "mytonic" seizures. A tonic-clonic seizure is the classic and most visible type of seizure associated with epilepsy and refers to a seizure in which the patient loses consciousness, the body stiffens, the patient falls to and experiences jerking movements, "Absence" seizures are generally characterized by momentary unconsciouness; "atonic" seizures are characterized by sudden loss of muscle control that causes person to fall to the ground); and "mytonic" seizures are characterized by brief forceful jerks by the whole body or part of it. Partial seizures are generally classified as "simple partial" (symptoms include twitching; numbness; sweating; dizziness; nausea; disturbances to hearing, vision, smell or taste; strong sense of déjà vu), or "complex partial" (the person appears aware when in fact he/she is not). It is often difficult to distinguish between these types of seizures in the clinic because rarely does the seizure occur in the doctor's office, and the patient usually has no memory of the seizure.

A single seizure, or even a plurality of seizures, does not mean that the person has epilepsy. Many young children have seizures that are not technically caused by epilepsy, such as convulsions from fevers. Other types of non-epileptic seizures are caused by an imbalance of body fluids or chemicals, prenatal brain impairment, or are associated with other disease states such as heart conditions and diabetes. These non-epileptic seizures are often referred to as "pseudo-epilepsy." They are often difficult to distinguish from epileptic seizures because of the multitude of forms that a seizure can take. Seizures can also often be caused by a condition known as non-epileptic attack disorder ("NEAD"). Seizures occurring in this condition are psychogenic in nature, and do not have a physical origin.

There are number of different procedures, including electroencephalogram (EEG) and brain scans (i.e. computed tomography) to determine whether a person has epilepsy and, if so, what kind of seizures the person has. Even with these advanced procedures, it is often very difficult to accurately differentiate between epilepsy and non-epilepsy, or to distinguish between the different types of epileptic seizures. Individuals suffering from pseudo-epilepys are often diagnosed as having epilepsy based upon EEG testing, and paroxysmal discharges observed in these patients during the test period. Among seizure patients who display abnormal paroxysmal discharges during testing, a method is needed for distinguishing between epilepsy and non-epilepsy.

Up-to-now there has been an unmet diagnostic need for an in vitro diagnostic test for distinguishing epilepsy from pseudo-epilepsy. There has also been an unmet diagnostic need for evaluating the risk of a person developing epilepsy, and for improved targeting, monitoring and adjustment of therapeutic regimens such as anticonvulsant medication and neurosurgery that are directed against epilepsy.

OBJECTS OF THE INVENTION

Therefore, it is an object of the invention to provide clinical utility of blood test and based on immunosorbent and immunochemical methods and kits for diagnosing central nervous system disorders such as paroxysmal cerebral discharges and epilepsy.

It is another object of the present invention to improve upon the accuracy of currently available methods for diagnosing paroxysmal cerebral discharges and epilepsy, and to improve diagnostic certainty of brain related seizures to the exclusion of non-epileptic seizures.

Yet another object is to provide assays for detecting free GluR1 peptide fragments in biological samples, not bound in immunoglobulin complexes.

It is still another object of the present invention to provide methods of diagnosing paroxysmal cerebral discharges and epilepsy using brain markers that distinguish between epilepsy and pseudo-epilepsy.

Still another object of the invention is to provide immunoassays and immunochemical blood analyses of the risk and progression of paroxysmal cerebral discharges and epilepsy, or the seizures resulting from brain damage.

It is another object of the present invention to provide rapid immunoassays and kits for diagnosing paroxysmal cerebral discharges and epilepsy, to provide real-time assessments of brain related seizures that permit effective therapeutic intervention.

It is another object of the present invention to provide rapid and inexpensive immunoassays and kits for diagnosing paroxysmal cerebral discharges and epilepsy, which can be performed at frequent intervals to monitor the progression of brain related seizures, or the effectiveness of anticonvulsant therapy.

SUMMARY OF THE INVENTION

Methods for evaluating the origin and cause of seizures in patients who display abnormal paroxysmal discharges have been discovered that are based upon the presence and quantity of GluR1 peptides and fragments in the biological fluids of individuals that have experienced seizures. Heretofore EEG measurements of paroxysmal discharges, combined with clinical evaluations of patients, have constituted the "gold standard" for evaluating the origin of seizures in individuals. Because of the established relationship between paroxysmal discharges and epilepsy, seizure patients with abnormal paroxysmal spiking are commonly (and often erroneously) diagnosed as epileptic, and often prescribed anticonvulsant medication or even operated on unnecessarily when in fact the origin of the seizure is not paroxysmal.

The present inventors have developed methods, compositions and kits, based upon GluR1, for determining whether abnormal paroxysmal activity is truly the origin of a seizure, and for more accurately diagnosing and treating patients who experience seizures that do not have paroxysmal origins despite the existence of abnormal paroxysmal discharges, i.e. "pseudo-epileptic" conditions such as fainting, migraine, loss of consciousness or amnesia and febrile or temperature seizures (in children). Therefore, in a first embodiment the invention provides a method for determining the origin of seizures in patients diagnosed as having paroxysmal discharges comprising directly or indirectly assaying a biological fluid in said patients for the presence and quantity of GluR1 or an immunogenic fragment thereof.

The inventors have also discovered improved methods for treating seizure disorders that result from abnormal paroxysmal spiking. In particular, the inventors have determined that medication type, dose and frequency can be adjusted based upon GluR1 changes (or lack thereof) observed in patients treated with a given medication. The inventors have also discovered methods for evaluating the advisability of reducing or ceasing an anticonvulsant medicine based upon GluR1 changes observed when said medication is reduced or ceased. Whereas medication dosage has traditionally been adjusted in a trial and error fashion, based upon whether the individual suffers seizures or exhibit abnormal EEG activity after the change in medication, the present invention provides an in vitro test for measuring response to the medication adjustment, and for evaluating the risk of seizures resulting from the medication adjustment. Therefore, in another embodiment, the invention provides a method of treating epilepsy in a patient comprising (a) directly or indirectly assaying a biological fluid in said patient for changes in the quantity of GluR1 in a biological fluid, or a fragment or analogue thereof, in response to treatment with an initial dose of an anti-epilepsy medication or a cessation or decrease in dose of an anti-epileptic medication; and (b) altering or maintaining said dose based upon said changes.

The inventors have still further discovered methods for predicting the risk of future seizures having paroxysmal discharges as their origin. These methods are particularly applicable to patients at high risk for such seizures such as neonates, persons who have experienced traumatic brain injury, and individuals suffering from temporal lobe epilepsy, who can suffer tremendously when they experience seizures, but for whom anticonvulsant therapy is typically administered cautiously due to the risks associated with such therapy. Newborns with birth detects such as congenital heart defect are in particular need for monitoring according to the methods of the present invention because these patients often cannot be assessed using EEG, and because heart surgery during infancy is known to cause brain injury manifested as seizures, developmental delay and motor abnormalities (Bellinger et al., Circulation 1999, 100: 526-32). Stroke patients are another particularly suitable at-risk group inasmuch as cerebrovascular diseases are known to be a major cause of common epilepsy late in life (Cleary et al., Lancet 2004, 363: 1184-6). Thus in another embodiment the invention provides a method for diagnosing the probability of epilepsy in patients at risk for epilepsy comprising directly or indirectly assaying a biological fluid in said patient for the presence and quantity of GluR1 or a fragment thereof.

These methods are most particularly carried out in immunoassays using specific GluR1 sequences and antibodies raised against these sequences. Thus, in another embodiment the invention provides a method for diagnosing and/or treating epilepsy or paroxysmal discharges in a human patient comprising directly or indirectly assaying a biological fluid from said patient for the presence and quantity of the GluR1 of SEQ ID NO: 5 or 6 (as described below) or an immunogenic fragment or homolog thereof. In another embodiment the invention provides compositions, kits, reagents, calibrators and standards based upon said peptide sequences and antibodies against them.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

FIG. 1 shows that in a clinical study, the G1uR1 aAb concentration in blood samples of healthy children and those with non-epileptic neurological disorders depends on age and steady increases as children age from neonates to adolescents.

FIG. 2 shows that the detection of G1uR1 aAb concentrations in blood specimens from patients with epilepsy and epilepsy syndromes shows that independently from age group all children have significantly elevated amounts of G1uR1 aAb compared with that for controls.

FIG. 3 shows that the levels of G1uR1 aAb are significantly higher for patients with generalized type of seizures compared with that for partial ones.

FIG. 4 shows that the level of G1uR1 aAb in healthy patients measured by use of PA-ELISA test is 1.5±0.3 ng/mL and for patients with non-epileptic neurological disorders (NED) is 1.7±0.2 ng/mL, and G1uR1 aAb-positive patients with epilepsy have a mean concentration of 3.02±0.4 ng/L (range 2.1-4.1).

FIG. 5 shows that different control values for G1uR1 aAb are revealed for women (1.8±0.1 ng/mL) and men (1.5±0.1 ng/mL) in total control group and patients with epilepsy as well.

FIG. 6 shows the investigation of G1uR1 aAb values in patients with different seizures types and frequency.

DISCUSSION

The present invention may be understood more readily by reference to the following detailed description of preferred embodiments of the invention and the Examples included therein. Before the present methods and techniques are disclosed and described, it is to be understood that this invention is not limited to specific analytical or synthetic methods as such may, of course, vary. It is also to be understood that the terminology used herein is for the purpose of describing particular embodiments only and is not intended to be limiting.

DEFINITIONS AND USE OF TERMS

The biological sample is blood, blood plasma, blood serum, cerebrospinal fluid, saliva, perspiration or brain tissue. More preferably, the biological sample is a biological fluid. The biological fluid is blood serum and plasma.

An analogue of a protein, peptide, or polypeptide means a protein, peptide, or polypeptide that contains one or more amino acid substitutions, deletions, additions, or rearrangements. For example, it is well known in the art of protein biochemistry that an amino acid belonging to a grouping of amino acids having a particular size or characteristic (such as charge, hydrophobicity, and hydrophilicity) can often be substituted for another amino acid without altering the activity of the protein, particularly in regions of the protein that are not directly associated with biological activity. Thus, an analogue of a GluR1 receptor or fragment thereof is useful in the present invention if it includes amino acid substitutions, deletions, additions or rearrangements at sites such that antibodies raised against the analogue are still specific against the AMPA receptor or fragment.

Preferably, a GluR1 recombinant analogue has at least 80%, 85%, 90%, or 95% amino acid identity with naturally occurring AMPA receptor. Amino acid identity is defined by an analogue comparison between the recombinant analogue and naturally occurring AMPA receptor. The two amino acid sequences are aligned in such a way that maximizes the number of amino acids in common along the length of their sequences; gaps in either or both sequences are permitted in making the alignment in order to maximize the number of common amino acids. The percentage amino acid identity is the higher of the following two numbers: (1) the number of amino acids that the two polypeptides have in common with the alignment, divided by the number of amino acids in the GluR1 analogue or fragment thereof, multiplied by 100, or (2) the number of amino acids that the two polypeptides have in common with the alignment, divided by the number of amino acids in naturally occurring AMPA receptor or fragment thereof, multiplied by 100.

GluR1 derivatives, and derivatives of GluR1 fragments, are also useful in the present invention, and include naturally occurring AMPA and AMPA receptor analogues and fragments thereof that are chemically or enzymatically derivatized at one or more constituent amino acids, including side chain modifications, backbone modifications, and N- and C-terminal modifications, by for example acetylation, hydroxylation, methylation, amidation, phosphorylation or glycosylation. The term also includes GluR1 salts such as zinc GluR1 and ammonium GluR1.

A protein or peptide is measured "directly" in the sense that the protein or peptide is itself measured in the biological sample, as opposed to some other indirect measure of the protein or peptide such as antigenic fragments, analogs or derivatives of the protein or peptide, or antibodies to the protein or peptide.

An "antigen" is protein or peptide that evokes an immune response.

The term "antibody" is synonymous with "immunoglobulin," and includes naturally occurring human antibodies, polyclonal antibodies, and monoclonal antibodies. The term "antibody" is meant to include both the native antibody and biologically active and synthetic derivatives of antibodies, such as, for example, Fab', F(ab")$_2$ or Fv as well as single-domain and single-chain antibodies. A biologically active derivative of an antibody retains the ability to bind antigen.

The term "immunoassay" is the laboratory approach to detect directly or indirectly protein or peptide in the biological fluid by use of immunological reaction between antigen and antibody.

The term "calibrator" is used herein, with respect to immunoassays that measure antibodies to GluR1, refers to a solution of GluR1 antibodies containing a known amount of GluR1 antibodies and used for a calibration curve to quantify the concentration of antibodies in an unknown biological fluid.

The term "standard" is used herein, with respect to immunoassays that measure antibodies to GluR1, refers to a solution of GluR1 antibodies isolated and purified from human biological fluids in a suitable quantitative form to control the quality of reagents containing in an immunoassay kit of the present invention.

A "negative control" as used herein, with respect to immunoassays that measure GluR1 peptides or fragments directly in biological fluids, refers to GluR1 synthetic peptide or fragment thereof in a suitable quantitative form intended for use as an indicator of GluR1 concentrations in biological fluids from healthy individuals.

A "positive control" as used herein, with respect to immunoassays that measure GluR1 peptides or fragments directly in biological fluids, refers to GluR1 synthetic peptide or fragments thereof in a suitable quantitative form intended for use as an indicator of GluR1 concentrations in biological fluids from individuals suffering from epileptic paroxysmal discharges.

GENERAL DISCUSSION

The present invention derives from the realization that genetic or accidental increase of expression of AMPA receptors or GluR1 in the brain can be correlated with paroxysmal cerebral discharges to diagnose brain related seizures, non-brain related seizures, and psychogenic related seizure, and to distinguish between brain related seizures that result from paroxysmal discharges and those that do not. Recombinant GluR1 receptors that are abnormally expressed in the brain are quickly metabolized and, following penetration of the blood brain barrier, these metabolic destruction products enter the circulatory system. The immune system recognizes these peptides and protein fragments as foreign antigens and responds by generating antibodies to them. The rapid evaluation of these brain biomarkers in individuals will greatly enhance the confidence of physicians when diagnosing paroxysmal cerebral discharges and epilepsy, and significantly improve diagnostic certainty of brain related seizures and following up anticonvulsant therapy that can be administered. The data can be used independently of other diagnostic strategies, but preferably forms an integral part of a comprehensive diagnostic strategy employing conventional diagnostic techniques.

The data obtained from the GluR1 biomarkers, especially when combined with EEG or brain scan data, can also be used to monitor the efficacy of a treatment regime. It has surprisingly been found that the GluR1 peptide and antibodies to them provide real time evidence of neurotoxicity, and that reductions in levels of circulating GluR1 peptides or antibodies correspond well with reductions in neurotoxic mechanisms. By obtaining data at appropriate intervals using rapid laboratory techniques such as latex agglutination or lateral flow, one is able to monitor the progression of the episode in response to the anticonvulsant therapeutic regime.

Immunoassay techniques are generally preferred for measuring the proteins or peptides of the present invention, as discussed in greater detail herein, although other analytical techniques are also available as known to those skilled in the art, such as HPLC. The amino acid sequences of preferred GluR1 subunits, and antigenic fragments thereof, are recited in SEQ ID NO 5 and 6, and any fragment, analogue or derivative of these sequences can be employed in methods for directly detecting the receptors as long as sufficient antigenicity is maintained. However, when using immunoassays it has been found that the antigenic determinants are concentrated in the N-terminal domain of the GluR1, GluR2, GluR3, and GluR4 receptor subunits, and that antibodies raised against the N-terminal domains and fragments thereof should be employed for optimal test results. The inventors have sequenced the amino acid chain of the N-terminal domains for these receptors, and set forth the sequences as SEQ ID NOS. 1, 2, 3 and 4, respectively, at the end of this document.

Conventional methods can be used to prepare the antibodies. For example, by using a peptide of a GluR1 protein, polyclonal antisera or monoclonal antibodies can be made using standard methods. A mammal, (e.g., a mouse, hamster, or rabbit) can be immunized with an immunogenic form of the peptide (preferably the GluR1 receptor, an antigenic determinant of the GluR1 receptor, or an analogue or derivative thereof) which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be administered and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)]. Hybridoma cells can be screened immunochemically for production of antibodies specifically reactive with the peptide and the monoclonal antibodies can be isolated. Therefore, the invention also contemplates hybridoma cells secreting monoclonal antibodies with specificity for GluR1 proteins or fragments thereof as described herein.

The biological sample tested for the receptor or fragment can be derived from blood, urine, blood plasma, blood serum, cerebrospinal fluid, saliva, perspiration, or brain tissue. In a preferred embodiment, the biological sample is a blood sample. In an even more preferred embodiment the biological sample is a blood sample diluted to a ratio of from about 1:2 to about 1:32 (v:v).

The invention also relates to indirect methods for measuring levels of recombinant GluR1 (GluR1) peptide or fragments thereof. Thus, analytical techniques can be used to evaluate indirect measures of GluR1 peptide or fragments thereof, such as antibodies specific for the recombinant peptide, or cDNA that encodes for this peptide. In one embodiment, GluR1 peptide and antibodies are simultaneously measured to obtain a reading of the likelihood for seizure onset. Concentrations of higher than 50 or 100 pg/mL (higher than 50 pg/mL in infants) for GluR1, especially when combined with GluR1 antibodies concentration higher than 1.5 ng/ml for men, 1.8 ng/ml for women, 1.0 ng/ml for children, are remarkably predictive of the occurrence of paroxysmal cerebral discharges and epilepsy, and typically justify anticonvulsive therapy, especially when observed in patients who experience paroxysmal spiking as measured by EEG.

The proposed blood test based on immunosorbent antibodies to GluR1 was tested on the blood serum samples of more than 2300 patients during last seven years, the diagnoses being as follows: epilepsy (1650), brain paroxysmal activity including acute ischemic stroke (187), parkinsonism (148), schizophrenia (manic-depressive psychosis, cyclothymia) (147), Alzheimer's disease (44), drug abuse (morphine, cocaine, hashish) (117), as well as 2150 healthy persons, including cross analyses.

Methods of Treatment

The diagnostic methods of the present invention are particularly useful when employed in conjunction with treatment regimens that are directed against epileptic seizures. The methods are useful when initiating anticonvulsive therapy, reducing or ceasing the therapy, or considering neurosurgery. The methods are preferably performed in conjunction with additional diagnostic methods such as EEG.

Thus, for example, intractable epilepsy that warrants neurosurgery can be diagnosed by using EEG and GluR1 monitoring in combination. Neurosurgery may, for example, be warranted based upon the presence of paroxysmal spiking, and abnormally high profiles of concentrations of GluR1 or fragment thereof, that fail to respond to one or more anticonvulsive drug regimens.

The need to change anticonvulsive medications, or to increase the dose of a prescribed medication, can similarly be assessed based on the ability of a given drug regimen to reduce GluR1 levels, or to reduce those levels below a designated standard based upon population norms. A preferred designated standard is 100, 75 or 50 pg/ml of GluR1 fragment, and/or 2.0, 1.8, 1.5, or 1.0 ng/ml of GluR1 antibody, for adults, and 75, 50, or 35 pg/ml of GluR1 fragment, and/or 1.5, 1.0 or 0.8 ng/ml of GluR1 antibody for children.

In still another embodiment, the methods of the present invention are practiced in conjunction with the cessation or reduction of anticonvulsant therapy. GluR1 levels are monitored in response to the cessation or reduction, and said therapy is reverted to if GluR1 levels either increase or increase above the foregoing designated standards.

Novel Kits of the Present Invention

In another embodiment the invention provides kits for diagnosing central nervous system disorders such as paroxysmal cerebral discharges and epilepsy. Recombinant GluR1 antibodies or antigens may be incorporated into immunoassay diagnostic kits depending upon whether antibodies or GluR1 are being measured. A kit may include a composition comprising an antigen or antibody preparation. Both antibody and antigen preparations should preferably be provided in a suitable quantitative form, with antigen and/or antibody concentrations given for easy reference in quantitative applications.

The kits may also include an immunodetection reagent or label for the detection of specific immunoreaction between the provided antigen and/or antibody, as the case may be, and the diagnostic sample. Suitable detection reagents are well known in the art as exemplified by radioactive, enzymatic or otherwise chromogenic agents, which are typically employed in association with the antigen and/or antibody, or in association with a second antibody having specificity for first antibody. Thus, the reaction is detected or quantified by means of detecting or quantifying the label. Immunodetection reagents and processes suitable for application in connection with the novel methods of the present invention are generally well known in the art.

The reagents may also include ancillary agents such as buffering agents and protein stabilizing agents, e.g., polysaccharides and the like. The diagnostic kit may further include where necessary agents for reducing background interference in a test, agents for increasing signal, apparatus for conducting a test, calibration curves and charts, standardization curves and charts, and the like.

In a more particular aspect the invention relates to an immunosorbent containing antibodies to GluR1 or synthetic peptide GluR1, present in an ELISA or latex agglutination format. Thus, in one embodiment, the kit contains a microtiter plate comprising GluR1 or fragments thereof or antibodies to GluR1, and a human or synthetic calibrator. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme and non-enzyme substrates), agents for reducing background interference in a test, agents to increase the signal, apparatus for conducting a test, calibration and standardization information or instructions, and the like.

Calibration is typically accomplished by generating a standard curve from the measurement of samples of known value. Specimens with unknown levels of analyte are then measured and compared to the standard curve using mathematically derived relationships. The standard curve may be determined prior to or concurrently with analysis of the sample specimens, depending on the stability and reproducibility of the assay. In one embodiment, the invention is practiced with a kit comprising, as a calibrator or control, antibodies raised against the GluR1 fragment of SEQ ID NO: 5 or 6, or an immunogenic fragment, homolog or derivative thereof. In yet another embodiment the kit is manufactured against an antibody standard comprising a specific fraction of immunoglobulins G purified from human blood, optionally immunoglobulins of 95% purity that specifically bind the GluR1 peptide without significant cross-reaction with other glutamate receptor fragments or other neuroreceptors (e.g. D1, D2, D3, NMDAR, opiate, etc).

Latex Agglutination

A latex agglutination technique or lateral flow format has also been developed which dramatically increases the speed of diagnosis obtained by the methods of this invention, and thereby improves the diagnostic certainty. Latex agglutination assays have been described in Beltz, G. A. et al., in Molecular Probes: Techniques and Medical Applications, A. Albertini et al., eds., Raven Press, New York, 1989, incorporated herein by reference. In the latex agglutination assay, antibody raised against a particular biomarker is immobilized on latex particles. A drop of the latex particles is added to an appropriate dilution of the serum to be tested and mixed by gentle rocking of the card. With samples lacking sufficient levels of the biomarkers, the latex particles remain in suspension and retain a smooth, milky appearance. However, if biomarkers reactive with the antibody are present, the latex particles clump into visibly detectable aggregates.

An agglutination assay can also be used to detect biomarkers wherein the corresponding antibody is immobilized on a suitable particle other than latex beads, for example, on gelatin, red blood cells, nylon, liposomes, gold particles, etc. The presence of antibodies in the assay causes agglutination, similar to that of a precipitation reaction, which can then be detected by such techniques as nephelometry, turbidity, infrared spectrometry, visual inspection, colorimetry, and the like.

The term latex agglutination is employed generically herein to refer to any method based upon the formation of detectable agglutination, and is not limited to the use of latex as the immunosorbent substrate. While preferred substrates for the agglutination are latex based, such as polystyrene and polypropylene, particularly polystyrene, other well-known substrates include beads formed from glass, paper, dextran, and nylon. The immobilized antibodies may be covalently, ionically, or physically bound to the solid-phase immunoadsorbent, by techniques such as covalent bonding via an amide or ester linkage, ionic attraction, or by adsorption. Those skilled in the art will know many other suitable carriers for binding antibodies, or will be able to ascertain such, using routine experimentation.

The technique can be adapted for use in the detection of GluR1 receptors, antibodies, or any other suitable biomarker against central nervous system disorders. Using the latex agglutination technique, one is able to provide real-time biochemical diagnosis and monitoring of patients with epilepsy (within about 10 minutes), and thereby dramatically improve follow-up anticonvulsant treatment. This is surprising because these biomarkers are naturally occurring and, in contrast to viruses for which latex agglutination methods were originally developed, show much lower strengths of association with their corresponding antibodies.

Thus, in one embodiment, the method of measuring the GluR1 receptor, fragment therof, or other biomarker is by latex agglutination comprising: (i) contacting the biological sample with an agglutinating carrier that comprises an antibody to GluR1 or an antigenic determinant of GluR1, for a sufficient time period and under conditions to promote agglutination; and (ii) reading a signal generated from the agglutination; wherein the amount of signal detected correlates to the titer of biomarkers present in the sample.

The reaction is preferably read macroscopically against a dark background for a sufficient time period. The method preferably yields a clinically useful reading within about 30 minutes or less. It has been experimentally found that latex beads having a mean diameter of from about 0.25 to about 0.4 micrometers are particularly preferred in the practice of this invention. Latex beads can be prepared generally by adding antibodies to the target biomarker to a carrier solution that contains a 1% concentration (by weight) of latex beads, until the concentration of the antibodies in the carrier solution reaches about 2 mg/ml, and allowing the ingredients a sufficient time to covalently link, typically about 1 hour, in the presence of a linking agent such as glutaraldehyde.

In another embodiment the invention provides a latex agglutination kit that comprises: (1) latex beads that comprise GluR1 or fragments thereof or antibodies to GluR1, and (2) positive and negative controls.

Novel Compositions of the Invention

The methods of the present invention rely upon a series of novel compositions which themselves form a part of the invention. Thus, in one series of embodiments the invention provides a recombinant polypeptide fragment of the GluR1, GluR2, GluR3 and GluR4 subunits of AMPA receptor, comprising:

1. The N-terminal domain of the GluR1, SEQ ID NO. 1;
2. The N-terminal domain of the GluR2, SEQ ID NO. 2;
3. The N-terminal domain of the GluR3, SEQ ID NO. 3;
4. The N-terminal domain of the GluR4, SEQ ID NO. 4;
5. Recombinant GluR1, SEQ ID NOs. 5 and 6, or an antigenic fragment, analog, or derivative thereof In another series of embodiments the invention provides any of the foregoing polypeptides linked covalently to a distinct antigenic determinant, such as human serum albumin. In still another series of embodiments the invention provides any of the foregoing polypeptides linked to any of the immunosorbent materials discussed above. The immunosorbent can be in the form of a bead for latex agglutination, in the size ranges discussed above, or in the form of a synthetic plate for conventional immunoassay analysis. The polypeptide can be linked to the immunosorbent using any conventional means of linkage, including covalent linkage, ionic linkage, and adsorption.

In another series of embodiments the present invention relates to the novel monoclonal and polyclonal antibodies specific for and/or raised against the foregoing polypeptides, including the foregoing polypeptides linked to distinct antigenic determinants. Thus, in one embodiment the invention provides non-human antibodies against any of the foregoing peptides or polypeptides or antigenic fragment, analog, or derivative thereof. In another embodiment the invention provides immunosorbents to which such antibodies are linked.

Brief Description of the Sequence Listings

The features, aspects, and advantages of the present invention will become better understood with regard to the following sequence listings where, in the sequence the recited amino acid position numbering reflects that used throughout this document.

SEQ ID NO:1. Shows the Amino Acid Sequence of the Mature N-Terminal Domain of GluR1 Receptor Subunit, as Follows:

```
SEQUENCE LISTING
PEPTIDE   Homo sapiens glutamate receptor ionotropic, GluR1
Proc. Natl. Acad. Sci. U.S.A. 88: 7557-7561 (1991)
     19                      AN FPNNIQIGGL FPNQQSQEHA AFRFALSQLT EPPKLLPQID    60

61 IVNISDSFEM TYRFCSQFSK GVYAIFGFYE RRTVNMLTSF CGALHVCFIT PSFPVDTSNQ   120

121 FVLQLRPELQ DALISIIDHY KWQKFVYIYD ADRGLSVLQK VLDTAAEKNW QVTAVNILTT   180

181 TEEGYRMLFQ DLEKKKERLV VVDCESERLN AILGQIIKLE KNGIGYHYIL ANLGFMDIDL   240

241 NKFKESGANV TGFQLVNYTD TIPAKIMQQW KNSDARDHTR VDWKRPKYTS ALTYDGVKVM   300

301 AEAFQSLRRQ RIDISRRGNA GDCLANPAVP WGQGIDIQRA LQQVRFEGLT GNVQFNEKGR   360

361 RTNYTLHVIE MKHDSIRKIG YWNEDDKFVP AATDAQAGGD NSSVQNRTYI VTTILEDPYV   420

421 MLKKNANQFE GNDRYEGYCV ELAAEIAKHV GYSYRLEIVS DGKYGARDPD TKAWNGMVGE   480

481 LVYGRADVAV APLTITLVRE EVIDFSKPFM SLGISIMIKK PQKSKPGVFS FLDPLA
```

SEQ ID NO:2. Shows the Amino Acid Sequence of the N-Terminal Domain of GluR2 Subunit, as Follows:

```
SEQ ID NO:2
PEPTIDE   Homo sapiens glutamate receptor. ionotropic, GluR2
NeuroReport 5: 441-444 (1994)
     22                         VSSNSIQIG GLFPRGADQE YSAFRVGMVQ FSTSEFRLTP    60

61 HIDNLEVANS FAVTNAFCSQ FSRGVYAIFG FYDKKSVNTI TSFCGTLHVS FITPSFPTDG   120

121 THPFVIQMRP DLKGALLSLI EYYQWDKFAY LYDSDRGLST LQAVLDSAAE KKWQVTAINV   180

181 GNINNDKKDE MYRSLFQDLE LKKERRVILD CERDKVNDIV DQVITIGKHV KGYHYIIANL   240

241 GFTDGDLLKI QFGGANVSGF QIVDYDDSLV SKFIERWSTL EEKEYPGAHT TTIKYTSALT   300

301 YDAVQVMTEA FRNLRKQRIE ISRRGNAGDC LANPAVPWGQ GVEIERALKQ VQVEGLSGNI   360
```

-continued

```
361 KYDQNGKRIN YTINIMELKT NGPRKIGYWS EVDKMVVTLT ELPSGNDTSG LENKTVVVTT  420

421 ILESPYVMMK KNHEMLEGNE RYEGYCVDLA AEIAKHCGFK YKLTIVGDGK YGARDADTKI  480

481 WNGM
```

SEQ ID NO:3; Shows the Amino Acid Sequence of the N-Terminal Domain of GluR3 Subunit, as Follows:

```
SEQ ID NO:3
PEPTIDE  Homo sapiens glutamate receptor. ionotropic, GluR3
Biochim. Biophys. Acta 1219: 563-566 (1994)
 29                        GF PNTISIGGLF MRNTVQEHSA FRFAVQLYNT   60

61 NQNTTEKPFH LNYHVDHLDS SNSFSVTNAF CSQFSRGVYA IFGFYDQMSM NTLTSFCGAL  120

121 HTSFVTPSFP TDADVQFVIQ MRPALKGAIL SLLGHYKWEK FVYLYDTERG FSILQAIMEA  180

181 AVQNNWQVTA RSVGNIKDVQ EFRRIIEEMD RRQEKRYLID CEVERINTIL EQVVILGKHS  240

241 RGYHYMLANL GFTDILLERV MHGGANITGF QIVNNENPMV QQFIQRWVRL DEREFPEAKN  300

301 APLKYTSALT HDAILVIAEA FRYLRRQRVD VSRRGSAGDC LANPAVPWSQ GIDIERALKM  360

361 VQVQGMTGNI QFDTYGRRTN YTIDVYEMKV SGSRKAGYWN EYERFVPFSD QQISNDSASS  420

421 ENRTIVVTTI LESPYVMYKK NHEQLEGNER YEGYCVDLAY EIAKHVRIKY KLSIVGDGKY  480

481 GARDPETKIW NGMVGELVYG RADIAVAPLT ITLVREEVID FSKPLMSLGI SIMIKKPQKS  540

541 KPGVFSFLDP LA
```

SEQ ID NO:4; Shows the Amino Acid Sequence of the N-Terminal Domain of GluR4 Subunit, as Follows:

```
SEQ ID NO:4
PEPTIDE  Homo sapiens glutamate receptor. ionotropic, GluR4
Recept. Channels 3: 21-31 (1995)
 21                GAFPSSVQIG GLFIRNTDQE YTAFRLAIFL HNTAPNASEA   60

61 PFNLVPHVDN IETANSFAVT NAFCSQYSRG VFAIFGLYDK RSVHTLTSFC SALHISLITP  120

121 SFPTEGESQF VLQLRPSLRG ALLSLLDHYE WNCFVFLYDT DRGYSILQAI MEKAGQNGWH  180

181 VSAICVENFN DVSYRQLLEE LDRRQEKKFV IDCEIERLQN ILEQIVSVGK HVKGYHYIIA  240

241 NLGFKDISLE RFIHGGANVT GFQLVDFNTP MVTKLMDRWK KLDQREYPGS ETPPKYTSAL  300

301 TYDGVLVMAE TFRSLRRQKI DISRRGKSGD CLANPAAPWG QGIDMERTLK QVRIQGLTGN  360

361 VQFDHYGRRV NYTMDVFELK STGPRKVGYW NDMDKLVLIQ DVPTLGNDTA AIENRTVVVT  420

421 TIMESPYVMY KKNHEMFEGN DKYEGYCVDL ASEIAKHIGI KYKIAIVPDG KYGARDADTK  480

481 IWNGMVGELV YGKAEIAIAP LTITLVREEV IDFSKPFMSL GISIMIKKPQ KSKPGVFSFL  540

541 DPLAYE
```

SEQ ID NO:5; Shows the Amino Acid Sequence of Recombinant GluR1, as Follows:

```
SEQ ID NO:5
PEPTIDE  Recombinant GluR1
LANLGFMDIDLNSGAVYGRAEIAGYCV
```

SEQ ID NO:6; Shows the Amino Acid Sequence of the Recombinant GluR1, Another Such Peptide (27 Amino Acids Derived from the GluR1 Sequence and an N-Terminal Cys for Attachment to a Carrier Protein) as Follows:

```
SEQ ID NO:6
PEPTIDE  Artificial Sequence
CN LANLGFMDIDLNSGAVYGRAEIAGYCV
```

EXAMPLES

Example 1

Clinical Assessment of Epilepsy in Children

This randomized and double-blinded trial was conducted at 4 Children Epilepsy Centers in Moscow and St. Petersburg (Russia) from, January 1995 through December 1999. Although our study is not strictly population-based, we recruited individuals to achieve a group representative of children with epilepsy in the western part of the country.

Eligible for the trials patients were at 4 mo.-14 years of age and had been diagnosed with epilepsy syndromes and seizures that were classified based on all information available at diagnosis and according to International League Against Epilepsy's (ILAE) guidelines by four pediatric epilepsy specialists. These include the localization-related and generalized idiopathic syndromes (e.g., benign rolandic and childhood absence epilepsy), and the cryptogenic and symptomatic generalized syndromes. The symptomatic and cryptogenic localization-related epilepsies represent a broad spectrum of syndromes defined by cause and localization, to the extent that these are known. The outcome in this group was mixed.

Etiology was classified separately from syndrome although it partially depends on the syndrome. Remote symptomatic refers to the presence of an underlying neurologic condition or insult associated with an increased risk of epilepsy (e.g., history of bacterial meningitis, stroke, cerebral palsy). Idiopathic syndromes are almost always assigned an idiopathic etiology. Occasionally, a neurologic abnormality coexists with an idiopathic syndrome (e.g., childhood absence epilepsy with mental retardation), in which case the etiology as remote symptomatic despite the idiopathic syndrome was classified. Results of neuroimaging studies were used in classifying etiology. Cryptogenic etiology refers to epilepsy that does not meet the criteria for an idiopathic syndrome and for which there is no identified significant underlying neurologic abnormality or condition. Such individuals appear to be otherwise neurologically normal.

Initial seizure frequency was defined as the ratio of the total number of unprovoked seizures since epilepsy diagnosis divided by the time between the dates of first unprovoked seizure and formal diagnosis. The seizure frequency was presented as 1 seizure per day to 1-2 fits per year. The follow up calls and observations for GluR1 aAb levels vs. seizures occurrence where performed through 7 days and 6 months (optional).

A definite diagnosis of epilepsy was based on two witnessed and well-described seizures onset or one witnessed and well-described seizure plus either EEG tracing or MRI/CT scan with evidence of a focal abnormality consistent with localization-related epilepsy.

Patients were excluded from the trial for nonepileptic seizures (e.g., pseudoseizures) or a treatable cause of seizures; progressive or degenerative disorder; psychiatric or mood disorder requiring medication, suicide attempt.

Children with non-epileptic neurological disorders and healthy individuals represented in age- and gender-matched groups where used as controls.

The trial was conducted in accordance with the international rules of good clinical practice. Written informed consent was obtained from each patient's parent or legal guardian before trial-related procedures were initiated.

Chi-square and t-tests were used for bivariate comparisons. Log transformations were employed when necessary to normalize a highly skewed distribution. For some continuous variables, categories were constructed to facilitate presentation of data and testing of the assumption of linearity.

A total of 605 children (age of 4 mo.-14 years, 302 girls and 303 boys) were recruited into the study. The initial age at onset was 1-2 years. The median follow-up was 1.0 year.

In this clinical study GluR1 aAb concentration in blood samples of healthy children and those with non-epileptic neurological disorders depended on age and steady increased as children aged from neonates to adolescents (FIG. 1). It is possibly due to developing immune system and to increase of naturally circulating autoantibodies during maturation. The amounts of GluR1 aAb differ insignificantly for healthy controls and children with non-epileptic disorders (FIG. 1). The comparison of mean values of GluR1 aAb in independent, age- and gender-matched groups demonstrated that aAb values for the healthy children, and patients with other neurological disorders belong to the same distribution with mean value of 0.9-1.1 ng/mL.

The detection of GluR1 aAb concentrations in blood specimens from patients with epilepsy and epilepsy syndromes showed that independently from age group all children had significantly elevated amounts of GluR1 aAb compared with that for controls (FIG. 2). Autoantibody levels were higher for children with age of 4 mo.-3 years when the most patients had the first unprovoked seizures and were diagnosed as having epilepsy or epi-syndromes. Pediatric patients at age of 3-14 years demonstrated decreased levels of GluR1 aAb compared with those at smaller age (FIG. 2).

The levels of GluR1 aAb were significantly higher for patients with generalized type of seizures compared with that for partial ones (FIG. 3). Significant correlation of spiking activity on EEG and GluR1 aAb concentrations (Spearman's coefficient 0.89, $p<0.01$) was demonstrated in all study centers. It was established that measuring GluR1 aAb in children have two potential uses: 1) epilepsy risk assessment; and 2) to assist to better clinical diagnosis of a patient with 'epilepsy like' symptoms. This premise is supported by the high predictive value of the test for recognizing individuals with epilepsy and epi-syndromes (84% at 1.0 ng/mL cutoff).

Clinically predetermined cutoff for GluR1 aAb allowed us to differentiate patients according to seizures frequency. Monitoring of GluR1 aAb in 41 patients with epilepsy within 1 month of hospital admission showed that GluR1 aAb levels (2.6-2.7 ng/mL) at frequency of seizures 1 per day or week were higher than that (2.2 ng/mL) at seizures frequency 1 per month. The tendency maintained the same for patients with epilepsy and epi-syndromes independently from age and type of seizures.

It was established the correlation of GluR1 aAb with data obtained from CT and MRI scans that were interpreted by neuroradiologists blinded to test results for children with intractable seizures assigned for neurosurgery. Maximal concentrations of GluR1 aAb in patient with right hemispheric localization of epileptic focus were detected (Iatsuk et al., Zh. Nevropat. Psikhiat. Im. SS Korsakova. 1999, 99:34-6). The etiology of disease affects on appearance of increased GluR1 aAb levels: prenatal trauma (100% cases), history of bacterial meningitis (85.8% cases) and tumor (55.6% cases).

The follow up investigation (6 mo.) of anti-epileptic therapy, seizures frequency, changes of EEG and GluR1 aAb in 19 children with mix type of seizures resulted in good correlation of detected parameters. The improvement of patient state (declining or absence of seizures) accompanied by down-regulation of GluR1 up to the control level in 84% of cases. The correlation of EEG data with GluR1 aAb values was about 95% in this study.

Example 2

Clinical Assessment of Adult Epilepsy

Double-blinded trial was conducted at Dept. of Epilepsy, V.M Bechterev's Institute on Psychiatry and Neurology and Dept. of Neurology, Russian Military Medical Academy in St. Petersburg (Russia) from February 1994 to December 1997. Two hundred thirty seven consecutive patients with epilepsy aged 18 to 40 years (130 women, 107 men) admitted to hospitals of aforementioned institutions due to increased frequency of seizures were considered for participation. Epilepsy was classified according to ILAE guidelines and the following inclusion criteria were considered in the protocol: the duration of disorder from 1 year to 20 years; the frequency of seizures from 1 per day to one per a year; type of seizures: partial simple, partial multiple, generalized with absences, generalized tonic-clonic of different etiology (e.g., history of bacterial meningitis, stroke, cerebral palsy, prenatal trauma etc.). A definite diagnosis of epilepsy was based on well-described history of seizures plus either EEG or MRI/CT scan with evidence of a focal abnormality consistent with localization-related epilepsy. Patients were excluded from the trial for progressive or degenerative disorder; psychiatric or mood disorder requiring medication, suicide attempt.

Patients (n=193, 79 women, 114 men) with non-epileptic neurological disorders (brain trauma without seizures, low back pain, arachnoidid), nonepileptic seizures (e.g., pseudoseizures) and healthy individuals (n=93) represented in age- and gender-matched groups to epileptic patients where used as controls.

The level of GluR1 aAb in healthy patients measured by use of PA-ELISA test was 1.5±0.3 ng/mL and for patients with non-epileptic neurological disorders (NED) was 1.7±0.2 ng/mL (FIG. 4). The comparison of mean values of GluR1 aAb in independent, age- and gender-matched groups demonstrated that aAb values for the control and patients with non-epileptic neurological disorders belong to the same distribution. GluR1 aAb-positive patients with epilepsy had a mean concentration of 3.02±0.4 ng/L (range 2.1-4.1). Different control values for GluR1 aAb were revealed for women (1.8±0.1 ng/mL) and men (1.5±0.1 ng/mL) in total control group and patients with epilepsy as well (FIG. 5).

Our studies demonstrated the increased amount of autoantibodies to glutamate binding proteins of healthy volunteers who have had instable spiking activity on EEG (25% of tested cases). These results indicate that the raised level of autoantibodies to both fragments of glutamate receptors might be blood marker of cerebrovascular abnormalities registered by EEG without any neurological signs. In addition, cross-reaction of both autoantibodies to NMDA and AMPA receptors was revealed in some cases of patients (32%) with epilepsy and stroke (Dambinova et al. J. Neurol. Sci. 1997, 152: 93-7).

It was demonstrated negative correlation between the duration of disease and value of GluR1 aAb (Odinak et al., Zh Nevropatol Psikhiatr Im S S Korsakova. 1996, 96: 45-48). Patients with duration of epilepsy less than 5 years had higher levels of GluR1 aAb then those with longer term of disease.

The investigation of GluR1 aAb values in patients with different seizures types and frequency is depicted in FIG. 6. The highest GluR1 concentrations were registered in patients with daily generalized tonic-clonic and partial multiple types of seizures in more than 86% cases. In patients with rare fits, less than 1 per a half year, increased above cut-off aAb value (1.5±0.3 ng/mL for all adults) was detected in more than 80% cases (Odinak et al. Zh Nevropatol Psikhiatr Im S S Korsakova. 1996, 96: 45-48; Gromov et al., Zh Nevropatol Psikhiatr Im S S Korsakova 1997, 97:46-9). The correlation of seizures frequency only with concentration of GluR1 aAb was not high as expected: Spearman's coefficient 0.34 ($p<0.01$).

The comparison of results from GRACE-NeuroTest-Epilepsy ELISA test with appearance of spiking activity on EEG allowed diagnose epilepsy and support epileptic nature of spiking activity in range 84%-95% cases (Odinak et al., Zh Nevropatol Psikhiatr Im S S Korsakova. 1996, 96: 45-48).

The investigation of time course prior and following seizures occurrence was performed in collaboration with Dr. J. Majkowsky (Clinic of Epilepsy, Warsaw, Poland, 1994-1995) and Dr. P. Wolf (Epilepsy Center, Bielefield, Germany, 1995-1996). It was demonstrated the sudden increase of GluR1 aAb prior seizures manifestations and aAb values maintained the on high level during the followed day. These results were supported by increased spiking activity defined by daily EEG

Example 3

GRACE-NeuroTest-Epilepsy ELISA Tests Performance

The GRACE-NeuroTest-Epilepsy ELISA kits for detecting GluR1 antibodies comprises (i) an immunosorbent for GluR1 peptide or antibodies to GluR1; and (ii) an indicator reagent comprising secondary antibodies attached to a signal-generating compound. The test intended to be used to assess persons undergoing paroxysmal cerebral discharges and epilepsy.

The quality of microplates covered by GluR1 peptide or antibodies to GluR1 was controlled by use of calibrators and sera specimens from healthy persons in presence and absence of calibrators (Gromova et al., Neirokhimiia. 1997, 1:23-7). The assessments of intra-assay variability, batch-to-batch variation and stability of the ELISA reaction for antibody or GluR1 calibrators were performed at various storage conditions (temperature, type of packing, storage duration). Kinetic of reaction was studies to reach optimal characteristics of variables. The concentrations of GluR1 peptide or GluR1 antibodies were then assessed in blood serum or plasma samples from patients with neurological disorders (stroke, Parkinson's and Alzheimer's diseases, palsies, and multiple sclerosis), infection diseases (TB, encephalitis, meningitis), non-infection disorders (phenylketonuria, lupus erythromatosis, diabetes, drug abuse) and healthy volunteers collected according to approved human investigative protocol.

Linearity

Blood specimens from four apparently healthy individuals were spiked with GluR1 antibodies to final concentrations of 200 ng/mL (serum) or GluR peptide to final concentration of 2.0 ng/mL (plasma). Each spiked specimen was diluted gravimetrically with unspiked one to obtain GluR1 antibodies or GluR1 peptide values throughout the range of GRACE-NeuroTest-Epilepsy assay. A correction was made for the small amount (<0.1 ng/mL for antibodies and <10 pg/mL for peptide) of endogenous GluR1 antibodies or GluR1 peptide in the unspiked sample. Linear regression analysis of the data indicates that the assays have linear range of 0-2.5 ng/mL for the GluR1 antibodies test and of 0-200 pg/mL.

Analytical Sensitivity

The analytical sensitivity or lowest detectable concentration that is distinguishable from zero for the GRACE-NeuroTest-Epilepsy ELISA was determined by testing a zero calibrator 20 times each using 4 lots of reagents on 5 days. The average 95% confidence limit of the analytical sensitivity of the GluR1 antibodies test was less than 0.05 ng/mL (95% confidence interval 0.01-0.06 ng/mL) and GluR1 peptide test was less than 5 pg/mL (95% confidence interval 0.2-4.9 pg/mL).

Interfering Substances

Hemoglobin (up to 10,000 mg/dL) and lipids (cholesterol up to 1000 mg/dL and triglycerides up to 1000 mg/dL) or bilirubin (up to 20 mg/dL) added to serum specimens containing GluR1 antibodies or GluR1 peptide did not interfere with the recovery of GluR1 antibodies or GluR1 peptide. However, severely hemolyzed specimens should be avoided whenever possible. When a sample appears to be severely hemolyzed, another specimen (serum or plasma) should be obtained and tested.

Analytical Specificity

Antibodies

The immunoactive peptides from N-terminal fragments of μ- (MOR) or δ-opioid receptors (DOR), glutamate receptors (NR1, GluR4), and dopamine receptors (D2, D3, D4) or their specific antibodies (IgG) were evaluated for potential cross-reactivity and interference in the GRACE-NeuroTest-Epilepsy ELISA assay at the concentrations indicated below. There was no significant interference with the GluR1 antibodies measurement, nor was there any significant assay cross-reactivity.

| Neuroreceptor Type | Concentration of Substance | | % Recovery | Reference |
| --- | --- | --- | --- | --- |
| | Antibodies, μg/mL | Peptide, ng/mL | | |
| MOR | 1.0 | 100 | 105% | Dambinova, Izykenova, 2002 |
| DOR | 1.0 | 100 | 107% | Dambinova, Izykenova, 2002 |
| GluR4 | 0.5 | 100 | 99% | Dambinova et al., 1997 |
| NR1 | 0.5 | 100 | 101% | Izykenova et al., 2000 |
| D2 | 1.0 | 100 | 104% | fragment 8-31 |
| D3 | 1.0 | 100 | 109% | fragment 6-27 |
| D4 | 1.0 | 100 | 103% | fragment 1-18 |

Example 4

GRACE-NeuroTest-Epilepsy Tests Results Deviation

Within-day and total imprecision were determined using the ANOVA model by testing controls and human specimen pools that had the respective analytes added at concentrations near the decision points of the assay and throughout the range of the standard curve. The study was conducted over 20 days, testing each control 5 times per day.

Average Intra-Assay Imprecision

| Mean | | Standard Deviation | | Coefficient of variation | |
| --- | --- | --- | --- | --- | --- |
| GluR1 Antibodies, ng/mL | GluR1 Peptide, pg/mL | GluR1 Antibodies, ng/mL | GluR1 Peptide, pg/mL | GluR1 Antibodies, % | GluR1 Peptide, % |
| 1.5 | 50 | 0.1 | 3.0 | 7.0 | 6.0 |
| 3.2 | 100 | 0.2 | 5.0 | 6.5 | 5.0 |
| 12.5 | 500 | 0.5 | 23.0 | 6.0 | 4.6 |

Average Inter-Assay Imprecision

| Mean | | Standard Deviation | | Coefficient of variation | |
| --- | --- | --- | --- | --- | --- |
| GluR1 Antibodies, ng/mL | GluR1 Peptide, pg/mL | GluR1 Antibodies, ng/mL | GluR1 Peptide, pg/mL | GluR1 Antibodies, % | GluR1 Peptide, % |
| 1.5 | 50 | 0.2 | 6.9 | 13.0 | 14.0 |
| 3.2 | 100 | 0.3 | 11.2 | 9.5 | 11.2 |
| 12.5 | 500 | 0.8 | 49.4 | 6.5 | 9.9 |

Example 5

GRACE-NeuroTest-Epilepsy ELISA Expected Values in Individuals Without Epilepsy

The circulating GluR1 peptide and GluR1 antibodies concentration were determined in blood specimens from 214 children (age of 4 mo.-14 years, 111 girls and 103 boys) and 286 individuals (126 women and 160 men) without epilepsy. This population included individuals with neurological disorders (brain trauma without seizures, low back pain, arachnoidid, Parkinson's and Alzheimer' diseases, pseudoepilepsy), infection diseases (TB, encephalitis, meningitis), non-infection disorders (phenylketonuria, lupus erythromatosis, diabetes, drug abuse) and healthy volunteers. There are no statistically significant changes in GluR antibodies concentration associated with brain trauma without seizures, low back pain, arachnoidid, phenylketonuria, lupus erythromatosis, drug abuse, TB, encephalitis, and meningitis. The descriptive statistics for GluR1 antibodies concentrations in individuals without epilepsy are shown in the following table. The values are representative of the values obtained from clinical studies. The decision threshold was determined by the 95% confidence limit of GluR1 antibodies concentration in the non-epilepsy population different ages. These values translate into a general specificity of the test of greater than 89% for GluR1 antibodies and greater than 92% for GluR1, i.e. less than 10% expected false positives in individuals without epilepsy.

GluR1 Antibodies Concentration (ng/mL) in Non-Epilepsy Population

| | All | | | | |
| --- | --- | --- | --- | --- | --- |
| | Children | | | Adults, Age 18-40 | |
| Index | Age <1 | Age 1-3 | Age 3-14 | Women | Men |
| Mean | 0.70 | 1.02 | 1.25 | 1.8 | 1.5 |
| SD | 0.15 | 0.34 | 0.29 | 0.1 | 0.2 |
| Median | 0.60 | 0.93 | 1.1 | 1.7 | 1.4 |
| Percent < 1.0 ng/mL | 99.0% | 98.0% | 96% | — | 5% |
| <1.5 ng/mL | — | — | 3% | 5% | 89% |
| <1.8 ng/mL | — | — | — | 90% | 2% |
| Minimum | 0.5 | 0.5 | 0.5 | 1.0 | 0.9 |
| Maximum | 0.9 | 1.2 | 1.4 | 1.9 | 1.5 |
| N | 70 | 81 | 63 | 126 | 160 |

GluR1 Peptide Concentration (pg/mL) in Non-Epilepsy Population

|  | All | | |
| --- | --- | --- | --- |
|  | Children | | Adults, Age 18-40 |
| Index | Age <3 | Age 3-14 | Women/Men |
| Mean, pg/mL | 45.2 | 84 | 97 |
| SD | 5.1 | 7.7 | 8.2 |
| Median | 48.3 | 89.5 | 99 |
| Percent | | | |
| <50 pg/mL | 94.0% | 1.0% | 0.5% |
| <100 pg/mL | 3.0% | 96.5% | 92.1% |
| Minimum | 38.2 | 75.3 | 88.4 |
| Maximum | 51.0 | 92.0 | 106.1 |
| N | 151 | 63 | 286 |

Based on routinely EEG and clinical evaluation the diagnosis and progression of epilepsy can only partially be predicted. Up-to-now there was an unmet diagnostic need for a laboratory test with blood samples. The GRACE-NeuroTest-Epilepsy gives an answer to this need. It is recommended to use this blood test support for all neurological considerations with respect to the differential diagnosis of epilepsy. The GRACE-NeuroTest-Epilepsy assay has been evaluated and is proposed for the following clinical indications in children:
  Rule in brain related seizures and epilepsy to increase the degrees of diagnosis certainty
  Rule out pseudo-epilepsy and epilepsy-like disorders.
  Reference ranges in blood: (Iatsuk et al. Zh Nevropat Psikhiat. SS Korsakova 1999, 99:34-6)

|  | Normal reference ranges | | |
| --- | --- | --- | --- |
| Children, age dependent | GluR1 antibody ng/mL | GluR1 peptide pg/mL | Antibody/peptide ratio |
| <3 years old | <0.7 | <50 | <14 |
| Between 3 and 14 years | <1.0 | <90 | <11 |

The GRACE-NeuroTest-Epilepsy Assay has been evaluated and is proposed for the following clinical indications in adults:
  Rule in brain related seizures and epilepsy to increase the degrees of diagnosis certainty
  Risk factor for paroxysmal cerebral discharges and epilepsy after other disorders
  Prognosis of brain related seizures
  Follow-up after treatment and for the adjustment of the adequate therapy and doses
  Reference ranges in serum: (Gromov et al. Zh Nevropatol Psikhiatr Im S S Korsakova 1997, 97:46-49)

|  | Normal reference ranges | | |
| --- | --- | --- | --- |
| Adult | GluR1 antibody ng/mL | GluR1 peptide pg/mL | Antibody/peptide ratio |
| Men | <1.5 | <100 | <15 |
| Women | <1.8 | <100 | <18 |

Example 6

GRACE-NeuroTest-Epilepsy ELISA Expected Values in Individuals With Epilepsy

Blood samples were obtained from 391 children (age of 4 mo.-14 years, 191 girls and 200 boys) and 237 individuals (130 women and 107 men) with epilepsy and epilepsy syndromes. The descriptive statistics for GluR1 aAb concentrations in patients with epilepsy and epilepsy syndromes are presented in the table below. These values are representative of the values obtained from clinical studies.

GluR1 Antibodies Concentration (ng/mL) in Patients with Epilepsy and Epi-Syndromes

|  | All | | | | |
| --- | --- | --- | --- | --- | --- |
|  | Children | | | Adults, Age 18-40 | |
|  | Age <1 | Age 1-3 | Age 3-14 | Women | Men |
| Mean | 2.0 | 2.5 | 2.8 | 3.2 | 2.7 |
| SD | 0.2 | 0.3 | 0.3 | 0.2 | 0.2 |
| Median | 1.9 | 2.2 | 2.6 | 2.7 | 2.4 |
| Percent > 1.0 ng/mL | 16% | 2% | 3% | 2% | 2% |
|  | 57% | 59% | 55% | 3% | 4% |
| >1.5 ng/mL | 21% | 34% | 37% | 90% | 88% |
| >1.8 ng/mL | | | | | |
| Minimum | 1.0 | 1.0 | 1.0 | 1.0 | 1.0 |
| Maximum | 2.4 | 3.0 | 3.3 | 4.1 | 3.1 |
| N | 119 | 132 | 140 | 130 | 107 |

GluR1 Peptide Concentration (pg/mL) in Patients with Epilepsy and Epilepsy Syndromes

|  | All | | |
| --- | --- | --- | --- |
|  | Children | | Adults, Age 18-40 |
| Index | Age <3 | Age 3-14 | Women/Men |
| Mean, pg/mL | 298.2 | 307.1 | 452.9 |
| SD | 91.1 | 146.4 | 152.2 |
| Median | 304.3 | 332.0 | 490.4 |
| Percent | | | |
| >50 pg/mL | 91.0% | 1.5% | 3% |
| >100 pg/mL | 8.0% | 96.5% | 93.2% |
| Minimum | 48.2 | 47.5 | 99.0 |
| Maximum | 495.4 | 481.0 | 905.2 |
| N | 251 | 140 | 237 |

Example 7

The Sensitivity and Specificity of GRACE-NeuroTest-Epilepsy ELISA

The 2 by 2 table for entire children groups assessed by GRACE-NeuroTest-Epilepsy assay detecting GluR antibodies

|  | Epi | No Epi | |
|---|---|---|---|
| Positive | 330 (TP) | 10 (FP) | 340 |
| Negative | 61 (FN) | 204 (TN) | 265 |
|  | 391 | 214 | 605 |

Total
Sensitivity: 330/391 = 84%
Specificity: 204/214 = 95%

The 2 by 2 table for entire children groups assessed by GRACE-NeuroTest-LA assay detecting GluR peptide

|  | Epi | No Epi | |
|---|---|---|---|
| Positive | 379 (TP) | 11 (FP) | 390 |
| Negative | 12 (FN) | 203 (TN) | 215 |
|  | 391 | 214 | 605 |

Total
Sensitivity: 379/391 = 97%
Specificity: 203/214 = 95%

The 2 by 2 table for entire adult groups assessed by GRACE-NeuroTest-Epilepsy assay detecting GluR antibodies

|  | Epi | No Epi | |
|---|---|---|---|
| Positive | 204 (TP) | 26 (FP) | 230 |
| Negative | 33 (FN) | 260 (TN) | 293 |
|  | 237 | 286 | 523 |

Total
Sensitivity: 204/237 = 86%
Specificity: 260/286 = 91%

The 2 by 2 table for entire adult groups assessed by GRACE-NeuroTest-LA assay detecting GluR peptide

|  | Epi | No Epi | |
|---|---|---|---|
| Positive | 221 (TP) | 21 (FP) | 242 |
| Negative | 16 (FN) | 265 (TN) | 281 |
|  | 237 | 286 | 523 |

Total
Sensitivity: 221/237 = 93%
Specificity: 265/286 = 93%

Example 8

Interpretation of Results
GRACE-NeuroTest-Epilepsy ELISA

The Receiver Operating Characteristic Curve (ROC) of GluR1 antibodies cut-offs versus clinical sensitivity and specificity provided the area under the curve >0.95±0.01 and cut-offs of 1 ng/mL for children (age<14 years), of 1.5 ng/mL for men and of 1.8 ng/mL for women. ROC of GluR1 peptide cut-offs versus clinical sensitivity and specificity provided the area under the curve >0.97±0.01 and cut-offs of 50 pg/mL for children (age<3 years) and of 100 pg/mL for adolescent and adults. The clinical sensitivity and specificity of the GRACE-NeuroTest-Epilepsy Test using set cutoffs for various age and gender groups is described in the table below.

Sensitivity and Specificity vs. Age & Gender

|  | All | | | |
|---|---|---|---|---|
|  | Children | | Adult, age 18-40 | |
| Index | GluR antibodies | GluR peptide | GluR antibodies | GluR peptide |
| Sensitivity, % | 84.0 | 97.0 | 85.0 | 93.0 |
| at 95% CI | 78.0-88.5 | 95.4-99.1 | 83.3-95.5 | 90.4-96.2 |
| Specificity, % | 95.0 | 95.0 | 91.0 | 93.0 |
| at 95% CI | 93.5-98.0 | 92.1-97.7 | 85.2-98.7 | 89.9-95.4 |

Clinical Specificity

Serum samples from persons without paroxysmal cerebral discharges and epilepsy were assayed for the presence of GluR1 antibodies. Total specificity was shown to be 91% for adult and 95% for children.

Clinical Sensitivity

The clinical sensitivity of the GluR1 antibodies assay to assess patients with epilepsy in a random population was determined to be 84-85%.

The clinical sensitivity of the assay for epilepsy was determined by comparing GluR1 test results from seven groups of selected patients: with epilepsy, both definite and uncertain; with loss of consciousness; fainting/syncope; migraine; brain trauma; and cerebrovascular disease.

TABLE

GluR1 Peptide Assay Clinical Performance

| Disease | Number of patients | Number of correct "+" results | Number of false "−" results | Clinical Sensitivity** % | Clinical Specificity %¶ |
|---|---|---|---|---|---|
| Epilepsy: Definite | 976* | 839 | 137 | 75 | — |
| Uncertain | 136* | 106 | 30 | 10 | — |
| Loss of consciousness | 32 | 31 | 1 | — | 100 |
| Fainting/syncope | 19 | 16 | 3 | — | 100 |
| Migraine | 17 | 13 | 4 | — | 99 |
| Traumatic Brain | 71* | 59 | 12 | — | 99 |

TABLE-continued

GluR1 Peptide Assay Clinical Performance

| Disease | Number of patients | Number of correct "+" results | Number of false "−" results | Clinical Sensitivity** % | Clinical Specificity %¶ |
|---|---|---|---|---|---|
| Injury Cerebrovascular disease: | | | | | |
| Stroke | 31 | 27 | 4 | — | 99 |
| TIA | 14 | 12 | 2 | — | 100 |
| Brain Tumor | 19* | 14 | 5 | — | 100 |
| Parkinsonism | 30 | 28 | 2 | — | 100 |
| Alzheimer's Disease | 15 | 12 | 3 | — | 100 |
| Multiple sclerosis | 15 | 15 | 0 | — | 100 |
| Other Diseases: | | | | | |
| TB | 18 | 18 | 0 | — | 100 |
| Phenylketonuria | 19 | 19 | 0 | — | 100 |
| Lupus erythromatosis | 31* | 31 | 0 | — | 100 |
| | 21* | 19 | 2 | — | 100 |
| Diabetes mellitus | 33* | 32 | 1 | — | 100 |
| Drug Abuse Healthy Persons | 505* | 461 | 44 | — | 95 |
| Total | 2002 | 1754 | 248 | 85 | 91 |

Example 9

GRACE-NeuroTest-Epilepsy LA

A rapid assay of GluR1 peptide for epilepsy assessment based on a latex agglutination technique directed on improvement of power of diagnostic certainty.

The GRACE-NeuroTest-Epilepsy LA assay employs triple concave slides with a built-in magnification device to detect the reaction visually, providing an immediate "yes" or "no" response. In this assay, plasma samples are mixed with antibody coupled with colored latex particles and agglutination is indicated in between 2 and 5 minutes. The reaction occurs in a homogeneous phase and can be detected visually:

antigen+latex-antibody→→→{latex-antibody←antigen}

We are developing the GRACE-NeuroTest-Epilepsy Flow microassay based on lateral-flow technique using colored latex particles containing antibodies to GluR1. The blood or plasma "reconstitutes" the latex-reagent and transports it to the detection line. In most cases, sandwich assays are performed. The test is a heterogeneous assay; ie, reactions in both solution and solid phase occur. This test procedure is as follows:

Step 1. Blood is dropped on a specific site on the lateral-flow device.
Step 2. Blood reconstitutes the colored latex reagent.
Step 3. If the analyte in question is in blood, then the first reaction takes place:
Antigen is bound to the antibody on the latex particle→→{antigen→antibody-latex}-complex.
Step 4. In parallel with the reaction in Step 3, transport to the detection line of the complex: {antigen→antibody-latex} with another antibody occurs. The following reaction then takes place:
{antigen→antibody-latex}→→alignment with second antibody The concentration of this complex can be quite high at the detection line and may be visually detected (ie, by color) or measured by device (fluorometric method). The analytical sensitivity is high because of the concentration-process of the colored particle (the "catching principle"). Healthy people generally have GluR1 peptide concentration of 50 pg/mL.

Clinical trials of GRACE-NeuroTest-Epilepsy in ELISA and LA formats combined with clinical observations and EEG data demonstrated its value. This could be shown very impressively by the comparison of the pre- and post-test probabilities of epilepsy in observed patient groups:

| Diagnostic Indication | | Pre-test probability of seizures and spiking activity on EEG, % | GluR1 antibodies LR* | GluR1 peptide LR* | Post-test Probability**, % |
|---|---|---|---|---|---|
| Epilepsy: | Definite | 63.5 | 9.4 | — | 83.5 (80, 95 CI) |
| | | | | 28.1 | 95.0 (90, 98 CI) |
| | Uncertain | 35.0 | 1.1 | — | 35.0 (21, 44 CI) |
| | | | | 5.0 | 42.0 (32, 51 CI) |
| Loss of consciousness | | 15.0 | <0.04 | — | 0.15 |
| | | | | <0.01 | <0.1 |
| Fainting/syncope | | 14.2 | <0.04 | — | 0.11 |
| | | | | <0.01 | <0.1 |
| Migraine | | <10 | 0.02 | — | <0.1 |
| | | | | <0.01 | <0.05 |

| Diagnostic Indication | Pre-test probability of seizures and spiking activity on EEG, % | GluR1 antibodies LR* | GluR1 peptide LR* | Post-test Probability**, % |
|---|---|---|---|---|
| Brain trauma | 32.3 | 0.9 | — | 3.5 |
|  |  | <0.01 |  | <0.02 |
| Stroke | 25.1 | 0.5 | — | 1.5 |
|  |  | <0.01 |  | <0.01 |

*Positive likelihood ratio, LR = Sensitivity/1 − Specificity;
**Post-test probabilities arrived from pre-test probabilities defined from clinical observations of seizure manifestations combined with EEG data and likelihood ratios (LR) for GluR1 autoantibodies positive test according to http://www.med.nagoya-cu.ac.jp/psych.dir/graphical.htm;
CI—confidence interval The latex agglutination method is especially well suited for POC use because GluR1 peptide levels are elevated at a very early stage of paroxysmal cerebral discharges and, thus provide real-time indication of neurotoxic events. In addition, results can be processed in less than 10 minutes, allowing timely and appropriate intervention.

This method provides reliable data in a format that is simple to interpret. The application of the latex agglutination technique to analysis of brain biomarkers for epilepsy will decrease the cost of analysis, provide the opportunity to monitor real-time progress of a treatment procedure, and allow physicians to determine the efficacy of medication administered in the treatment of epilepsy.

What is claimed is:

1. A method for determining whether paroxysmal activity is the origin of seizures in patients diagnosed as having paroxysmal discharges, thereby distinguishing between epileptic and pseudo-epileptic seizures, and treating patients suffering from seizures of paroxysmal origin, comprising directly measuring the presence and quantity of GluR1 by assaying a biological fluid in said patients for GluR1 and GluR1 fragments, correlating greater than a predetermined amount of GluR1 and GluR1 fragments with paroxysmal origin of said seizures and, when said origin is paroxysmal, further comprising:
   a) treating said patient with an initial dose of anticonvulsive drug therapy;
   b) directly assaying said biological fluid for the presence and quantity of GluR1;
   c) increasing the dose, changing the drug, or treating with multiple drugs, if the quantity of GluR1 fails to fall below the predetermined amount of GluR1 and GluR1 fragments; and
   d) employing, as a control or calibrator, the GluR1 fragment of SEQ ID NO: 5 or 6 wherein the predetermined amount is at least 50 pg/ml.

2. The method of claim 1, wherein the predetermined amount is 75 pg/ml.

3. The method of claim 1, wherein the predetermined amount is 100 pg/ml.

4. The method of claim 1 wherein said origin is paroxysmal or non-paroxysmal.

5. The method of claim 1 wherein said biological fluid is blood, urine, blood plasma, blood serum, cerebrospinal fluid, saliva, or perspiration, or a derivative thereof.

6. The method of claim 1 wherein said seizures are associated with pseudo-epileptic loss of consciousness, fainting, migraine, brain trauma, stroke, psychogenic activity, narcolepsy, Tourette syndrome, cardiac arrythmia, drug abuse or stroke.

7. The method of claim 1 further comprising comparing said quantity of GluR1 to a baseline level of GluR1 selected from population norms and prior levels measured in said patient.

8. The method of claim 1 wherein for a child under three years of age, a concentration of free GluR1 or fragment thereof in blood of greater than 50 pg/ml indicates a paroxysmal origin of said seizures, and a GluR1 concentration in blood of less than 50 pg/ml indicates a non-paroxysmal origin of said seizures.

9. The method of claim 1 wherein:
   a) said biological fluid is assayed for the presence and quantity of GluR1,
   b) said method is carried out using a diagnostic kit, and
   c) said kit comprises an antibody standard comprising a specific fraction of immunoglobulins G purified from human blood, optionally immunoglobulins of 95% purity that specifically bind the GluR1 peptide without significant cross-reaction with other glutamate receptor fragments or other neuroreceptors.

10. The method of claim 1 further comprising:
    a) analyzing said patient for paroxysmal spiking on EEG;
    b) clinically evaluating said patient for intractable epilepsy;
    c) performing neurosurgery on said patient based upon the presence of paroxysmal spiking, intractable epilepsy, and abnormally high profiles of concentrations of GluR1 or fragment thereof.

11. The method of claim 1 further comprising correlating changes in the presence or quantity of GluR1 to alterations in paroxysmal spiking activity as measured by EEG.

12. The method of claim 1 wherein the quantitating of GluR1 and GluR1 fragments is performed by direct ELISA, RIA, immunodot, immunoblot, latex agglutination, lateral flow, fluorescence polarization assay, or microarray.

13. The method of claim 1, comprising:
    a) contacting said biological sample with a solid phase comprising antibodies to GluR1 or a fragment thereof, for a time sufficient to form a complex between said antibodies and, if present in the biological sample, GluR1 or fragment thereof;
    b) contacting said complex with an indicator reagent attached to a signal-generating compound; and
    c) measuring the signal generated; wherein the amount of signal detected correlates to the amount of said GluR1 or fragment thereof present in said sample.

14. The method of claim 13, wherein said indicator reagent comprises chicken anti-human IgG attached to horseradish peroxidase.

15. The method of claim 1, wherein the biological sample is plasma or serum diluted to a ratio of about 1:50.

16. A method for determining whether paroxysmal activity is the origin of seizures in a patient diagnosed as having paroxysmal discharges, and thereby distinguishing between epileptic and pseudo-epileptic seizures, comprising:
    a) contacting a biological sample from said patient with immunosorbent substrate particles upon which are immobilized antibodies to GluR1 or a fragment thereof, wherein said contacting of said biological sample is for 10 minutes or less to form an agglutination complex between said antibodies and GluR1 or fragment thereof;
    b) reading a signal generated from the agglutination; wherein a signal that corresponds to a quantity of GluR1 and fragments thereof above a predetermined amount correlates to paroxysmal origin for said seizures; and
    c) employing, as a control or calibrator, the GluR1 fragment of SEQ ID NO: 5 or 6 wherein the predetermined amount is 50 pg/ml.

17. The method of claim 16, wherein the predetermined amount is 75 pg/ml.

18. The method of claim 16, wherein the predetermined amount is 100 pg/ml.

19. A method for determining whether paroxysmal activity is the origin of seizures in patients diagnosed as having paroxysmal discharges and distinguishing between epileptic and pseudo-epileptic seizures, comprising directly measuring the presence and quantity of GluR1 in a biological fluid from a patient suffering from seizures by assaying said biological fluid, further comprising employing, as a control or calibrator, the GluR1 fragment of SEQ ID NO: 5 or 6 wherein a finding that at least 50 pg/ml of GluR1 is present in the biological fluid indicates that the patient has paroxysmal origin of the seizures.

20. The method of claim 19, wherein a finding that at least 75 pg/ml of GluR1 is present in the biological fluid indicates that the patient has paroxysmal origin of the seizures.

21. The method of claim 19, wherein a finding that at least 100 pg/ml of GluR1 is present in the biological fluid indicates that the patient has paroxysmal origin of the seizures.

* * * * *

```
                         SEQUENCE LISTING

<160> NUMBER OF SEQ ID NOS: 6

<210> SEQ ID NO 1
<211> LENGTH: 518
<212> TYPE: PRT
<213> ORGANISM: Homo sapiens

<400> SEQUENCE: 1

Ala Asn Phe Pro Asn Asn Ile Gln Ile Gly Gly Leu Phe Pro Asn Gln
1               5                   10                  15

Gln Ser Gln Glu His Ala Ala Phe Arg Phe Ala Leu Ser Gln Leu Thr
            20                  25                  30

Glu Pro Pro Lys Leu Leu Pro Gln Ile Asp Ile Val Asn Ile Ser Asp
        35                  40                  45

Ser Phe Glu Met Thr Tyr Arg Phe Cys Ser Gln Phe Ser Lys Gly Val
    50                  55                  60

Tyr Ala Ile Phe Gly Phe Tyr Glu Arg Arg Thr Val Asn Met Leu Thr
65                  70                  75                  80

Ser Phe Cys Gly Ala Leu His Val Cys Phe Ile Thr Pro Ser Phe Pro
                85                  90                  95

Val Asp Thr Ser Asn Gln Phe Val Leu Gln Leu Arg Pro Glu Leu Gln
            100                 105                 110

Asp Ala Leu Ile Ser Ile Ile Asp His Tyr Lys Trp Gln Lys Phe Val
        115                 120                 125

Tyr Ile Tyr Asp Ala Asp Arg Gly Leu Ser Val Leu Gln Lys Val Leu
    130                 135                 140

Asp Thr Ala Ala Glu Lys Asn Trp Gln Val Thr Ala Val Asn Ile Leu
145                 150                 155                 160

Thr Thr Thr Glu Glu Gly Tyr Arg Met Leu Phe Gln Asp Leu Glu Lys
                165                 170                 175

Lys Lys Glu Arg Leu Val Val Val Asp Cys Glu Ser Glu Arg Leu Asn
            180                 185                 190
```

```
Ala Ile Leu Gly Gln Ile Ile Lys Leu Glu Lys Asn Gly Ile Gly Tyr
        195                 200                 205

His Tyr Ile Leu Ala Asn Leu Gly Phe Met Asp Ile Asp Leu Asn Lys
        210                 215                 220

Phe Lys Glu Ser Gly Ala Asn Val Thr Gly Phe Gln Leu Val Asn Tyr
225                 230                 235                 240

Thr Asp Thr Ile Pro Ala Lys Ile Met Gln Gln Trp Lys Asn Ser Asp
                245                 250                 255

Ala Arg Asp His Thr Arg Val Asp Trp Lys Arg Pro Lys Tyr Thr Ser
            260                 265                 270

Ala Leu Thr Tyr Asp Gly Val Lys Val Met Ala Glu Ala Phe Gln Ser
        275                 280                 285

Leu Arg Arg Gln Arg Ile Asp Ile Ser Arg Arg Gly Asn Ala Gly Asp
    290                 295                 300

Cys Leu Ala Asn Pro Ala Val Pro Trp Gly Gln Gly Ile Asp Ile Gln
305                 310                 315                 320

Arg Ala Leu Gln Gln Val Arg Phe Glu Gly Leu Thr Gly Asn Val Gln
                325                 330                 335

Phe Asn Glu Lys Gly Arg Arg Thr Asn Tyr Thr Leu His Val Ile Glu
            340                 345                 350

Met Lys His Asp Ser Ile Arg Lys Ile Gly Tyr Trp Asn Glu Asp Asp
        355                 360                 365

Lys Phe Val Pro Ala Ala Thr Asp Ala Gln Ala Gly Gly Asp Asn Ser
    370                 375                 380

Ser Val Gln Asn Arg Thr Tyr Ile Val Thr Thr Ile Leu Glu Asp Pro
385                 390                 395                 400

Tyr Val Met Leu Lys Lys Asn Ala Asn Gln Phe Glu Gly Asn Asp Arg
                405                 410                 415

Tyr Glu Gly Tyr Cys Val Glu Leu Ala Ala Glu Ile Ala Lys His Val
            420                 425                 430

Gly Tyr Ser Tyr Arg Leu Glu Ile Val Ser Asp Gly Lys Tyr Gly Ala
        435                 440                 445

Arg Asp Pro Asp Thr Lys Ala Trp Asn Gly Met Val Gly Glu Leu Val
    450                 455                 460

Tyr Gly Arg Ala Asp Val Ala Val Ala Pro Leu Thr Ile Thr Leu Val
465                 470                 475                 480

Arg Glu Glu Val Ile Asp Phe Ser Lys Pro Phe Met Ser Leu Gly Ile
                485                 490                 495

Ser Ile Met Ile Lys Lys Pro Gln Lys Ser Lys Pro Gly Val Phe Ser
            500                 505                 510

Phe Leu Asp Pro Leu Ala
        515

<210> SEQ ID NO 2
<211> LENGTH: 463
<212> TYPE: PRT
<213> ORGANISM: Homo sapiens

<400> SEQUENCE: 2

Val Ser Ser Asn Ser Ile Gln Ile Gly Gly Leu Phe Pro Arg Gly Ala
1               5                   10                  15

Asp Gln Glu Tyr Ser Ala Phe Arg Val Gly Met Val Gln Phe Ser Thr
                20                  25                  30

Ser Glu Phe Arg Leu Thr Pro His Ile Asp Asn Leu Glu Val Ala Asn
            35                  40                  45
```

```
Ser Phe Ala Val Thr Asn Ala Phe Cys Ser Gln Phe Ser Arg Gly Val
 50                  55                  60

Tyr Ala Ile Phe Gly Phe Tyr Asp Lys Lys Ser Val Asn Thr Ile Thr
 65                  70                  75                  80

Ser Phe Cys Gly Thr Leu His Val Ser Phe Ile Thr Pro Ser Phe Pro
                 85                  90                  95

Thr Asp Gly Thr His Pro Phe Val Ile Gln Met Arg Pro Asp Leu Lys
                100                 105                 110

Gly Ala Leu Leu Ser Leu Ile Glu Tyr Tyr Gln Trp Asp Lys Phe Ala
            115                 120                 125

Tyr Leu Tyr Asp Ser Asp Arg Gly Leu Ser Thr Leu Gln Ala Val Leu
130                 135                 140

Asp Ser Ala Ala Glu Lys Lys Trp Gln Val Thr Ala Ile Asn Val Gly
145                 150                 155                 160

Asn Ile Asn Asn Asp Lys Lys Asp Glu Met Tyr Arg Ser Leu Phe Gln
                165                 170                 175

Asp Leu Glu Leu Lys Lys Glu Arg Arg Val Ile Leu Asp Cys Glu Arg
            180                 185                 190

Asp Lys Val Asn Asp Ile Val Asp Gln Val Ile Thr Ile Gly Lys His
            195                 200                 205

Val Lys Gly Tyr His Tyr Ile Ile Ala Asn Leu Gly Phe Thr Asp Gly
210                 215                 220

Asp Leu Leu Lys Ile Gln Phe Gly Gly Ala Asn Val Ser Gly Phe Gln
225                 230                 235                 240

Ile Val Asp Tyr Asp Asp Ser Leu Val Ser Lys Phe Ile Glu Arg Trp
                245                 250                 255

Ser Thr Leu Glu Glu Lys Glu Tyr Pro Gly Ala His Thr Thr Thr Ile
            260                 265                 270

Lys Tyr Thr Ser Ala Leu Thr Tyr Asp Ala Val Gln Val Met Thr Glu
            275                 280                 285

Ala Phe Arg Asn Leu Arg Lys Gln Arg Ile Glu Ile Ser Arg Arg Gly
290                 295                 300

Asn Ala Gly Asp Cys Leu Ala Asn Pro Ala Val Pro Trp Gly Gln Gly
305                 310                 315                 320

Val Glu Ile Glu Arg Ala Leu Lys Gln Val Gln Val Glu Gly Leu Ser
                325                 330                 335

Gly Asn Ile Lys Phe Asp Gln Asn Gly Lys Arg Ile Asn Tyr Thr Ile
            340                 345                 350

Asn Ile Met Glu Leu Lys Thr Asn Gly Pro Arg Lys Ile Gly Tyr Trp
            355                 360                 365

Ser Glu Val Asp Lys Met Val Val Thr Leu Thr Glu Leu Pro Ser Gly
370                 375                 380

Asn Asp Thr Ser Gly Leu Glu Asn Lys Thr Val Val Val Thr Thr Ile
385                 390                 395                 400

Leu Glu Ser Pro Tyr Val Met Met Lys Lys Asn His Glu Met Leu Glu
                405                 410                 415

Gly Asn Glu Arg Tyr Glu Gly Tyr Cys Val Asp Leu Ala Ala Glu Ile
            420                 425                 430

Ala Lys His Cys Gly Phe Lys Tyr Lys Leu Thr Ile Val Gly Asp Gly
            435                 440                 445

Lys Tyr Gly Ala Arg Asp Ala Asp Thr Lys Ile Trp Asn Gly Met
450                 455                 460
```

<210> SEQ ID NO 3
<211> LENGTH: 524
<212> TYPE: PRT
<213> ORGANISM: Homo sapiens

<400> SEQUENCE: 3

```
Gly Phe Pro Asn Thr Ile Ser Ile Gly Gly Leu Phe Met Arg Asn Thr
1               5                   10                  15

Val Gln Glu His Ser Ala Phe Arg Phe Ala Val Gln Leu Tyr Asn Thr
            20                  25                  30

Asn Gln Asn Thr Thr Glu Lys Pro Phe His Leu Asn Tyr His Val Asp
        35                  40                  45

His Leu Asp Ser Ser Asn Ser Phe Ser Val Thr Asn Ala Phe Cys Ser
    50                  55                  60

Gln Phe Ser Arg Gly Val Tyr Ala Ile Phe Gly Phe Tyr Asp Gln Met
65                  70                  75                  80

Ser Met Asn Thr Leu Thr Ser Phe Cys Gly Ala Leu His Thr Ser Phe
                85                  90                  95

Val Thr Pro Ser Phe Pro Thr Asp Ala Asp Val Gln Phe Val Ile Gln
            100                 105                 110

Met Arg Pro Ala Leu Lys Gly Ala Ile Leu Ser Leu Leu Gly His Tyr
        115                 120                 125

Lys Trp Glu Lys Phe Val Tyr Leu Tyr Asp Thr Glu Arg Gly Phe Ser
    130                 135                 140

Ile Leu Gln Ala Ile Met Glu Ala Ala Val Gln Asn Asn Trp Gln Val
145                 150                 155                 160

Thr Ala Arg Ser Val Gly Asn Ile Lys Asp Val Gln Glu Phe Arg Arg
                165                 170                 175

Ile Ile Glu Glu Met Asp Arg Arg Gln Glu Lys Arg Tyr Leu Ile Asp
            180                 185                 190

Cys Glu Val Glu Arg Ile Asn Thr Ile Leu Glu Gln Val Val Ile Leu
        195                 200                 205

Gly Lys His Ser Arg Gly Tyr His Tyr Met Leu Ala Asn Leu Gly Phe
    210                 215                 220

Thr Asp Ile Leu Leu Glu Arg Val Met His Gly Gly Ala Asn Ile Thr
225                 230                 235                 240

Gly Phe Gln Ile Val Asn Asn Glu Asn Pro Met Val Gln Gln Phe Ile
                245                 250                 255

Gln Arg Trp Val Arg Leu Asp Glu Arg Glu Phe Pro Glu Ala Lys Asn
            260                 265                 270

Ala Pro Leu Lys Tyr Thr Ser Ala Leu Thr His Asp Ala Ile Leu Val
        275                 280                 285

Ile Ala Glu Ala Phe Arg Tyr Leu Arg Arg Gln Arg Val Asp Val Ser
    290                 295                 300

Arg Arg Gly Ser Ala Gly Asp Cys Leu Ala Asn Pro Ala Val Pro Trp
305                 310                 315                 320

Ser Gln Gly Ile Asp Ile Glu Arg Ala Leu Lys Met Val Gln Val Gln
                325                 330                 335

Gly Met Thr Gly Asn Ile Gln Phe Asp Thr Tyr Gly Arg Arg Thr Asn
            340                 345                 350

Tyr Thr Ile Asp Val Tyr Glu Met Lys Val Ser Gly Ser Arg Lys Ala
        355                 360                 365

Gly Tyr Trp Asn Glu Tyr Glu Arg Phe Val Pro Phe Ser Asp Gln Gln
    370                 375                 380
```

```
Ile Ser Asn Asp Ser Ala Ser Ser Glu Asn Arg Thr Ile Val Val Thr
385                 390                 395                 400

Thr Ile Leu Glu Ser Pro Tyr Val Met Tyr Lys Lys Asn His Glu Gln
            405                 410                 415

Leu Glu Gly Asn Glu Arg Tyr Glu Gly Tyr Cys Val Asp Leu Ala Tyr
        420                 425                 430

Glu Ile Ala Lys His Val Arg Ile Lys Tyr Lys Leu Ser Ile Val Gly
            435                 440                 445

Asp Gly Lys Tyr Gly Ala Arg Asp Pro Glu Thr Lys Ile Trp Asn Gly
        450                 455                 460

Met Val Gly Glu Leu Val Tyr Gly Arg Ala Asp Ile Ala Val Ala Pro
465                 470                 475                 480

Leu Thr Ile Thr Leu Val Arg Glu Glu Val Ile Asp Phe Ser Lys Pro
            485                 490                 495

Leu Met Ser Leu Gly Ile Ser Ile Met Ile Lys Lys Pro Gln Lys Ser
        500                 505                 510

Lys Pro Gly Val Phe Ser Phe Leu Asp Pro Leu Ala
            515                 520

<210> SEQ ID NO 4
<211> LENGTH: 526
<212> TYPE: PRT
<213> ORGANISM: Homo sapiens

<400> SEQUENCE: 4

Gly Ala Phe Pro Ser Ser Val Gln Ile Gly Gly Leu Phe Ile Arg Asn
1               5                   10                  15

Thr Asp Gln Glu Tyr Thr Ala Phe Arg Leu Ala Ile Phe Leu His Asn
            20                  25                  30

Thr Ala Pro Asn Ala Ser Glu Ala Pro Phe Asn Leu Val Pro His Val
        35                  40                  45

Asp Asn Ile Glu Thr Ala Asn Ser Phe Ala Val Thr Asn Ala Phe Cys
    50                  55                  60

Ser Gln Tyr Ser Arg Gly Val Phe Ala Ile Phe Gly Leu Tyr Asp Lys
65                  70                  75                  80

Arg Ser Val His Thr Leu Thr Ser Phe Cys Ser Ala Leu His Ile Ser
            85                  90                  95

Leu Ile Thr Pro Ser Phe Pro Thr Glu Gly Glu Ser Gln Phe Val Leu
            100                 105                 110

Gln Leu Arg Pro Ser Leu Arg Gly Ala Leu Leu Ser Leu Leu Asp His
        115                 120                 125

Tyr Glu Trp Asn Cys Phe Val Phe Leu Tyr Asp Thr Asp Arg Gly Tyr
    130                 135                 140

Ser Ile Leu Gln Ala Ile Met Glu Lys Ala Gly Gln Asn Gly Trp His
145                 150                 155                 160

Val Ser Ala Ile Cys Val Glu Asn Phe Asn Asp Val Ser Tyr Arg Gln
            165                 170                 175

Leu Leu Glu Glu Leu Asp Arg Arg Gln Glu Lys Lys Phe Val Ile Asp
        180                 185                 190

Cys Glu Ile Glu Arg Leu Gln Asn Ile Leu Glu Gln Ile Val Ser Val
    195                 200                 205

Gly Lys His Val Lys Gly Tyr His Tyr Ile Ile Ala Asn Leu Gly Phe
    210                 215                 220

Lys Asp Ile Ser Leu Glu Arg Phe Ile His Gly Gly Ala Asn Val Thr
```

-continued

```
                225                 230                 235                 240

Gly Phe Gln Leu Val Asp Phe Asn Thr Pro Met Val Thr Lys Leu Met
                245                 250                 255

Asp Arg Trp Lys Lys Leu Asp Gln Arg Glu Tyr Pro Gly Ser Glu Thr
            260                 265                 270

Pro Pro Lys Tyr Thr Ser Ala Leu Thr Tyr Asp Gly Val Leu Val Met
        275                 280                 285

Ala Glu Thr Phe Arg Ser Leu Arg Arg Gln Lys Ile Asp Ile Ser Arg
    290                 295                 300

Arg Gly Lys Ser Gly Asp Cys Leu Ala Asn Pro Ala Ala Pro Trp Gly
305                 310                 315                 320

Gln Gly Ile Asp Met Glu Arg Thr Leu Lys Gln Val Arg Ile Gln Gly
                325                 330                 335

Leu Thr Gly Asn Val Gln Phe Asp His Tyr Gly Arg Arg Val Asn Tyr
            340                 345                 350

Thr Met Asp Val Phe Glu Leu Lys Ser Thr Gly Pro Arg Lys Val Gly
        355                 360                 365

Tyr Trp Asn Asp Met Asp Lys Leu Val Leu Ile Gln Asp Val Pro Thr
    370                 375                 380

Leu Gly Asn Asp Thr Ala Ala Ile Glu Asn Arg Thr Val Val Thr
385                 390                 395                 400

Thr Ile Met Glu Ser Pro Tyr Val Met Tyr Lys Lys Asn His Glu Met
                405                 410                 415

Phe Glu Gly Asn Asp Lys Tyr Glu Gly Tyr Cys Val Asp Leu Ala Ser
            420                 425                 430

Glu Ile Ala Lys His Ile Gly Ile Lys Tyr Lys Ile Ala Ile Val Pro
        435                 440                 445

Asp Gly Lys Tyr Gly Ala Arg Asp Ala Asp Thr Lys Ile Trp Asn Gly
    450                 455                 460

Met Val Gly Glu Leu Val Tyr Gly Lys Ala Glu Ile Ala Ile Ala Pro
465                 470                 475                 480

Leu Thr Ile Thr Leu Val Arg Glu Glu Val Ile Asp Phe Ser Lys Pro
                485                 490                 495

Phe Met Ser Leu Gly Ile Ser Ile Met Ile Lys Lys Pro Gln Lys Ser
            500                 505                 510

Lys Pro Gly Val Phe Ser Phe Leu Asp Pro Leu Ala Tyr Glu
        515                 520                 525

<210> SEQ ID NO 5
<211> LENGTH: 27
<212> TYPE: PRT
<213> ORGANISM: Homo sapiens

<400> SEQUENCE: 5

Leu Ala Asn Leu Gly Phe Met Asp Ile Asp Leu Asn Ser Gly Ala Val
1               5                   10                  15

Tyr Gly Arg Ala Glu Ile Ala Gly Tyr Cys Val
            20                  25

<210> SEQ ID NO 6
<211> LENGTH: 29
<212> TYPE: PRT
<213> ORGANISM: Homo Sapiens
```

-continued

```
<400> SEQUENCE: 6

Cys Asn Leu Ala Asn Leu Gly Phe Met Asp Ile Asp Leu Asn Ser Gly
1               5                   10                  15

Ala Val Tyr Gly Arg Ala Glu Ile Ala Gly Tyr Cys Val
            20                  25
```